(12) United States Patent
Coupland

(10) Patent No.: US 6,670,526 B1
(45) Date of Patent: Dec. 30, 2003

(54) ARABIDOPSIS ESD4 GENE AND METHOD TO CONTROL FLOWERING TIME

(75) Inventor: George M. Coupland, Norwich (GB)

(73) Assignee: Plant Bioscience Limited, Norwich (GB)

( * ) Notice: Subject to any disclaimer, the term of this patent is extended or adjusted under 35 U.S.C. 154(b) by 0 days.

(21) Appl. No.: 09/445,774

(22) PCT Filed: Jun. 12, 1998

(86) PCT No.: PCT/GB98/01714

§ 371 (c)(1),
(2), (4) Date: Mar. 8, 2000

(87) PCT Pub. No.: WO98/56918

PCT Pub. Date: Dec. 17, 1998

(30) Foreign Application Priority Data

Jun. 13, 1997 (GB) .............................................. 9712415

(51) Int. Cl.⁷ ......................... C12N 15/29; C12N 15/82; C12N 15/90; A01H 5/00; A01H 5/10
(52) U.S. Cl. ................... 800/290; 435/320.1; 435/419; 435/468; 435/471; 536/23.6; 800/298
(58) Field of Search .............................. 435/69.1, 320.1, 435/410, 419, 468, 471; 536/23.6; 800/260, 278, 285, 286, 290, 295, 298

(56) References Cited

FOREIGN PATENT DOCUMENTS

WO  WO 97/10339  3/1997  ........... C12N/15/29

OTHER PUBLICATIONS

Jean–Marc Neuhaus et al., High—level expression of a tobacco chitinase gene *Nicotiana sylvestris*. Susceptibility of transgenic plants to *Cercospora nicotianae* infection, Plant Molecular Biology, 16, pp. 141–151.*

Soon–Kee Sung et al., Molecular Cloning and Characterization of a MADS–Box cDNA Clone of the Fuji Apple. Plant Cell Physiol. 38 (4), pp. 484–489.*

Greg M. Arndt et al., Colocalization of antisense RNAs and ribozymes with their target mRNAs, Genome 40, pp. 785–797.*

Simon and Coupland, "Arabidopsis genes that regulate flowering time in response to day–length", Cell & Developmental Biology 7:419–425 (1996).

Zagotta et al, "Early–flowering Mutants of *Arabidopsis thaliana*", Aust. J. Plant Physiol 19:411–18 (1992).

Martinez–Zapater et al, "The Transition to Flowering in Arabidopsis", Arabidopsis, pp. 403–433 (1994), Cold Spring Harbor Laboratory Press.

Aubourg et al, "Structure, organization and putative function of the genes identified within a 23.9–kb fragment from *Arabidopsis thaliana* chromosome IV" Gene 199 (1/2):241–253 (1997).

* cited by examiner

*Primary Examiner*—Ashwin D. Mehta
(74) *Attorney, Agent, or Firm*—Nixon & Vanderhye P.C.

(57) ABSTRACT

The EARLY SHORT DAYS 4 gene ESD4 of Arabidopsis thaliana, and homologues from other species, and manipulation and use thereof in plants to influence timing of flowering of the plants.

19 Claims, 6 Drawing Sheets

Fig. 1

```
   1 AGAACCCTAATTTCATGTTCTAGGTGTCTCTCGAATGGTTCTCATCTCATTGATTACTCA   60
  61 ATCTCTAGGGTTTAGTGGTTCATCCAAATTCGTACCCTAATGGGTGCCGTAGCGATCAAT  120
                                           M  G  A  V  A  I  N
 121 CGTAAACGCAGCGACGAATCCTTCAATTTCATTAATCAACAATCAACCAACCCTTTACGA  180
      R  K  R  S  D  E  S  F  N  F  I  N  Q  Q  S  T  N  P  L  R
 181 AATTCACCGTATTTCCAAGCTTCCAAGAAACGAAGATTCTCATTCGCTATGTCTGAAGAT  240
      N  S  P  Y  F  Q  A  S  K  K  R  R  F  S  F  A  M  S  E  D
 241 TCTGGTAAGCCAGCGTCTTCAAACCCAACAATTTCGAGGATTTCAAGGTACCCTGATGCT  300
      S  G  K  P  A  S  S  N  P  T  I  S  R  I  S  R  Y  P  D  A
 301 AAAGCTCCTCTTAGACGAGAGATTCATGCTCCTAGTAGAGGAATTCTTAGATATGGAAAG  360
      K  A  P  L  R  R  E  I  H  A  P  S  R  G  I  L  R  Y  G  K
 361 GCAAAATCTAATGATTACTGCGAAAAGGACGCAAATTTCTTTGTTCGTAAGTATGATGAT  420
      A  K  S  N  D  Y  C  E  K  D  A  N  F  F  V  R  K  Y  D  D
 421 GCAAAGAGATCAGCTTTGGAAGCTTTGAGATTCGTTAATAAAGGTAAAGACTTTGTTGAT  480
      A  K  R  S  A  L  E  A  L  R  F  V  N  K  G  K  D  F  V  D
 481 TTGGGTGATGAGGTTGAAAAGGAGGAAGTTGTTTCTGATGATTCAAGTGTTCAAGCAATT  540
      L  G  D  E  V  E  K  E  E  V  V  S  D  D  S  S  V  Q  A  I
 541 GAAGTTATTGATTGTGATGATGATGAGGAGAAGAAGAATCTTCAGCCTTCGTTTTCTTCT  600
      E  V  I  D  C  D  D  D  E  E  K  K  N  L  Q  P  S  F  S  S
 601 GGTGTTACTGATGTTAAGAAAGGGGAGAACTTTAGAGTTGAGGATACTAGTATGATGCTG  660
      G  V  T  D  V  K  K  G  E  N  F  R  V  E  D  T  S  M  M  L
 661 GATTCGTTGTCGTTAGATAGAGATGTCGATAATGATGCTTCGAGCCTCGAAGCTTATAGA  720
      D  S  L  S  L  D  R  D  V  D  N  D  A  S  S  L  E  A  Y  R
 721 AAGCTTATGCAAAGTGCGGAGAAGAGGAATTCAAAGTTGGAAGCTTTGGGTTTTGAGATT  780
      K  L  M  Q  S  A  E  K  R  N  S  K  L  E  A  L  G  F  E  I
 781 GTGTTGAATGAGAAGAAGTTGTCACTGCTGCGTCAGTCTCGCCCAAAGACTGTGGAAAAG  840
      V  L  N  E  K  K  L  S  L  L  R  Q  S  R  P  K  T  V  E  K
 841 CGTGTTGAGGTGCCTCGTGAACCTTTTATTCCTCTCACAGAAGATGAAGAGGCTGAAGTC  900
      R  V  E  V  P  R  E  P  F  I  P  L  T  E  D  E  E  A  E  V
 901 TACCGTGCCTTTTCTGGGAGAAATAGAAGGAAGGTCTTGGCTACTCATGAAAACTCAAAC  960
      Y  R  A  F  S  G  R  N  R  R  K  V  L  A  T  H  E  N  S  N
 961 ATTGATATTACTGGAGAAGTTCTGCAATGCCTTACACCATCTGCATGGCTAAACGACGAG 1020
      I  D  I  T  G  E  V  L  Q  C  L  T  P  S  A  W  L  N  D  E
1021 GTTATCAATGTCTACCTTGAACTACTCAAAGAAAGAGAAACTAGAGAGCCCCCAAAGTAT 1080
      V  I  N  V  Y  L  E  L  L  K  E  R  E  T  R  E  P  P  K  Y
1081 TTGAAGTGTCTCTACTTCAATACCTTTTTCTACAAAAAGCTGGTAAGCGATTCTGGTTAT 1140
      L  K  C  L  Y  F  N  T  F  F  Y  K  K  L  V  S  D  S  G  Y
1141 AATTTTAAAGCTGTCAGGAGATGGACTACGCAGAGAAAGTTGGGATATGCTCTTATTGAC 1200
      N  F  K  A  V  R  R  W  T  T  Q  R  K  L  G  Y  A  L  I  D
1201 TGTGACATGATATTTGTTCCCATCCACAGGGGTGTGCATTGGACCTTGGCAGTAATTAAC 1260
      C  D  M  I  F  V  P  I  H  R  G  V  H  W  T  L  A  V  I  N
1261 AACAGGGAAAGCAAGCTCTTGTATCTTGATTCACTGAATGGAGTTGATCCTATGATTCTG 1320
      N  R  E  S  K  L  L  Y  L  D  S  L  N  G  V  D  P  M  I  L
1321 AATGCTCTGGCAAAATACATGGGTGATGAAGCAAATGAAAAAAGTGGAAAAAAGATTGAT 1380
      N  A  L  A  K  Y  M  G  D  E  A  N  E  K  S  G  K  K  I  D
1381 GCTAATTCGTGGGACATGGAATTTGTGGAAGACCTTCCCCAACAAAAGAATGGGTATGAC 1440
      A  N  S  W  D  M  E  F  V  E  D  L  P  Q  Q  K  N  G  Y  D
1441 TGTGGAATGTTTATGCTTAAGTACATCGATTTTTTCAGCAGAGGCCTGGGGCTATGTTTC 1500
      C  G  M  F  M  L  K  Y  I  D  F  F  S  R  G  L  G  L  C  F
1501 AGCCAGGAACACATGCCATACTTCCGACTCAGAACAGCTAAAGAGATTCTGAGGCTACGA 1560
      S  Q  E  H  M  P  Y  F  R  L  R  T  A  K  E  I  L  R  L  R
1561 GCTGATTGA 1569
      A  D  *
```

Fig. 2A

ESD4 genomic sequence.

```
   1 ACCAAAAAAATTTACCCTATGATCTATTATATATGAAACCATATTTCTAGAAAAATTTGA   60
  61 TTTCTTAATGTTTTGTGTTCATATATTTTATGATTTTACATAGATATTAAAGAAATAGAC  120
 121 AGAATAAATATATTTAGTCACGTAAAGTATTGGAATAATTAATGTATTTGATTTCACTTA  180
 181 GGATCTCTAATCTATTTCACTAGGATTTTCTTTCATGGTTGGGTTGGCACTGGCCTTTGA  240
 241 GATAAGATACGCATTCGTGTTTGGATGATGTTACCTTTCCACGCATTGAACAAGAGCTGC  300
 301 AACTTCAGAAACATTACCGTATCTATCACACGTGTCATCAACAAGGGTGAAGACTGTGTT  360
 361 GATCTTAGCTAGTGAAACTCTCCCAAGTGAAAATTGTGGCTCGAAATATATCATTATTGC  420
 421 AAATAAATAGCATTCGATCAATCTATCCCTGAAGTAAGGTGGGAGTTTAGATGCAAGGTC  480
 481 TTGCTGCTTCCACCATCTGCAAAACATGTCAATGACTATTGTCAACTTGTATCGCAAAAA  540
 541 ACATATAGCTAGAAGCACGAAAAATCTAGAGTATAGTACTTGGTCAGAGTTTTCAATTCT  600
 601 TGAATCCAATTTAGCTGCAAAAACTTGAAATTGATCTTGGCAAATCTAAGTAGCATCTTG  660
 661 TTGTGATCTTCTTCTTGTTCATAGAAAGAAATGTATTCCCTCGCGAATATCATTTCGGCA  720
 721 TTGTAATGTTGAGGCATGCAAAGAGCATTTCGTATACGCATTAAGATATGGGGAGAACTT  780
 781 GCTCCAGCTCTAGCTAACGACTCCAAGTTTCTTGTAGTGAAGCTTAACGCTTCCTCCAAG  840
 841 ATATCTTCTCTTGTTGTCCTTAAGTGAGCAGCTTCATACAAACTCACCATGCCCTTGACA  900
 901 TCACTGGTTATAGATTCCATAAACTTTTCATTCTCCCCTTTGAATCTCTTGAAAACATCT  960
 961 ATTGGTCAATAGGAGAATCTTGTTAATACATATGAATCGATTACAAAAAAATGTACTGGT 1020
1021 AGATAACTTTTACCGGTAGACATGTTGTAACCGTATGTCCTGAAAACCCAAAACATGATG 1080
1081 GAAATCGTGTACAAATCATCTTCACCGGCTATCATCTCCTGTATCTTTTCAAAACCCTCT 1140
1141 TCTAGACTCTGCTCAATCTCATCTTCAAAGTGAAACGCTACACCAAGGCTCACAAGCATA 1200
1201 TATATGAAAAGAATCCTCTTCTTGGTCGACTCAATGCTTTTCGAAGAAAACATGAGCATC 1260
1261 TCCCCTACTTCCGGCTTTAGTCTCTCAATCTCTTGGGCAAGGGCATTCATTTCCTAACAA 1320
1321 TAATATCATATGTTCATACCCGTTACATCGATCTTTTACATTTATTATATATATGTTTGT 1380
1381 CAGTGTGTATTATAGACTCACCGAGACATCAACTTGAGCAGAGAGGAAATGGTGACCCCA 1440
1441 TTTTGAAAGCGGCAGTCTCTTGAACTTGCGATTACTTTCTTGATCATGACAGGCCCGAGT 1500
1501 AGGGGTGGCCTTCATGCGAACAAGCTTTCCATGCTGACCTGAAAATGACTTGTGGGAAA 1560
1561 GCTAGAGAGTTTTCTTACCGAAAAATAAATTGGAACGTAAAGGAAGAGAGTATAGATCC 1620
1621 ATAAGCTGATATGCATTGCATGTTTACTACTAGTGATATGGAATACATTTTCACCACCAA 1680
1681 ATTTATAGGCAAAACATAAGCGTTTTCATTAAGTCATCTTTTGAAAAGTTTTGGAAGAAT 1740
1741 GTATATTAATACCCCATATTTATCTTCTTCAGTGTATAATACAACCTATGTTGGGACCA 1800
1801 TGATATTTTCTGAATTTATAGTGATATTAGTTTATCTTTAAATTGATATTTATTAATCTA 1860
1861 TATAGATCTTTTTTTAATTATTTAATTTTTTAAAGAATACGAGTTGACACAATTCAATAT 1920
1921 ACATCAAATTAATGACTTGGATGTTGAAATTTGTGTAGTATTAGAATTGAAAATTTAATA 1980
1981 TTTCAAAAAACTCATTTGACAATAAATCACAATGACTATAACTGAATTCATTTATATAAT 2040
2041 AGATATACATACATCTAAGTTTATGATTAATAACCTCAACTATCAGATTTTTAAATGTAG 2100
2101 TAGACTATTGAAATGAAAATAATGCAGATTAAGAAGTTGTATACTTATAAAAACTTATGA 2160
2161 CTAATTGTATTAGGAAGTTATAAACGATACTACAATATGATAGTTTTAAAACACAACATA 2220
2221 ATTTAATGAAAATTAGAGACAAAATCATTGTTTGATGTAATAATAGTTCAAGACAAACTC 2280
2281 TAACAAACATTCAATAGTTCAAAAAATATTTAAACTATAGATTATATATATTATCGTATA 2340
2341 TATATTATATTTTTGTGGTTATTAATTTATGATGTTATTAAAATCATATTTTTTATATAG 2400
2401 GGTTTTAAAAAATTGTTAACTTATTATTTTATCAAATTATGTTAAATTTTACATTCACAC 2460
2461 GACTTGAAACTAATATAATATTATCTCCTTGTATTTATTAATTTATCAAAAATTAATTTG 2520
2521 TAGAGGTTTTACTGTAAAACATGTTTAGTTTTTCATTTTTTAAAAAACCTCCAAGTGGCA 2580
2581 AAAATAAGATCCATCTCCATCTAAAAAAGTGCAAACAAATCTCCATCATTTAAAAAATCAA 2640
2641 CGTTAACATCCATATCTATTGTTGTTGTTTTTTACTTCTTTTTCTCTTGGTCAAACTCTA 2700
2701 CGTTAGTTTGATCAATAAATATGACAAGAATTTTTGCAGTCTCATAGGCGTCTTTGtaaa 2760
2761 ggttagttagcgtctacataattttccgaaagatataattttottgagatacagttaact 2820
2821 caattactgaaatgtaataactttctaaaagttgtggtattaaacaaaattgtgaaaaa 2880
2881 atttaaacaaaagccacttcaaaaacaaagaaaaccataaccattaatcaaaattcttt 2940
2941 tttttttgttaacaagtactagttgcattaaattgtaaacatatggtggtgttgtatatg 3000
3001 tttgatacaaagaacctatataacaaaggcttgttgggatagtgcatctgccacattatt 3060
3061 totttcogattgacatgtccatagatgagtgtgatagcttcaacatccaatatcgtata 3120
3121 ccaccaaagactgaagatagtaccaagaatatttatatatatatttatttattta 3180
3181 ttttggtaaggagaatatttatatcatgatcccaaccatactttaattgttatgaaaaat 3240
3241 tttaatttgatttttoataaatttttatagttttagttaagtataaaacaaaatttttttc 3300
3301 tttcaaatattatttttggagaaaaccccaaatttaaaaggaaagagaaaaatcaaat 3360
3361 cattcatctttgagatttotttttcttctacagaacctaatttcatgttctaggtgtctc 3420
3421 tcgaatggttctcatctcattgattactcaatctctagggtttagtggttcatccaaatt 3480
3481 cgtaccctaatgggtgcgtagcgatcaatogtaaacgCAGCGACGAATCCTTCAATTTC 3540
3541 ATTAATCAACAATCAACCAACCCTTTACGAAATTCACCGTATTTCCAAGCTTCCAAGAAA 3600
3601 CGAAGATTCTCATTCGCTATGTCTGAAGATTCTGGTAAGCCAGCGTCTTCAAACCCAACA 3660
3661 ATTTCGAGGATTTCAAGGTACCCTGATGCTAAAGCTCCTCTTAGACGAGAGATTCATGCT 3720
3721 CCTAGTAGAGGAATTCTTAGATATGGAAAGGCAAAATCTAATGATTACTGCGAAAAGGAC 3780
3781 GCAAATTTCTTTGTTCGTAAGTATGATGATGCAAAGAGATCAGCTTTGGAAGCTTTGAGA 3840
```

Fig. 2B

```
3841  TTCGTTAATAAAGGTAAAGACTTTGTTGATTTGGGTGATGAGGTTGAAAAGGAGGAAGTT  3900
3901  GTTTCTGATGATTCAAGTGTTCAAGCAATTGAAGTTATTGATTGTGATGATGATGAGGAG  3960
3961  AAGAAGAATCTTCAGCCTTCGTTTCTTCTGGTGTTACTGATGTTAAGAAAGGGGAGAAC   4020
4021  TTTAGAGTTGAGGATACTAGTATGATGCTGGATTCGTTGTCGTTAGATAGAGATGTCGAT  4080
4081  AATGATGCTTCGAGCCTCGAAGCTTATAGAAAGCTTATGCAAAGTGCGGAGAAGAGGAAT  4140
4141  TCAAAGTTGGAAGCTTTGGGTTTTGAGATTGTGTTGAATGAGAAGAAGTTGTCACTGCTG  4200
4201  CGTCAGTCTCGCCCAAAGACTGTGGAAAAGCGTGTTGAGGTGATGAGATTTATACTAATC  4260
4261  TTTCTTGAATTGGATATAATTAATGACATTGCTTTGTTTGGATTGTTTCTCTAAAATGCA  4320
4321  TATGATGTTATCGCCTACTGTTTGTTAGTGTAGACTGAAGATAGTACAATACTTGTTGGC  4380
4381  TTTATTGGTTATTAAGCTGCAGTTATTACTTATGCACACAGAGTCAAAGTTCTTCTACTT  4440
4441  ATTAGAGTATATTGTAATCTTAGCGTTGAGATCGTTAGTGTGTTTCTATGTTTATTGTTG  4500
4501  TTGTTAACACTATGTTTGTTGTTGATATAATGAAGGTGCCTCGTGAACCTTTTATTCCTC  4560
4561  TCACAGAAGATGAAGAGGCTGAAGTCTACCGTGCCTTTTCTGGGAGAAATAGGTATGGTT  4620
4621  CTTAAGACCTCTAGCATGTTGAGTGATTTTTTTTAGTCTAACCAAAAACCAAATGTCTCC  4680
4681  CATTTTCAGAAGGAAGGTCTTGGCTACTCATGAAAACTCAAACATTGATATTACTGGAGA  4740
4741  ACTTCTGCAATGCCTTACCCATCTGCATGGCTAAACACAAGTACACTTGTCCATAATATC  4800
4801  TACACATAAACTCTAAACCATTTCTTTGTGATTTCTTGTTCGTTTTATAGGTTATCAAT  4860
4861  GTCTACCTTGAACTACTCAAAGAAAGAGAAACTAGAGAGCCCAAAAAGTATTTGAAGTGT  4920
4921  CACTACTTCAATACCTTTTTCTACAAAAAGGTTTGTTTTCTTTCTGCTCAGATGATTTTT  4980
4981  AACAAAAATTTGATCCTTTTTGCCTCATGTCAGTTCGACTGAGTAGCTGCTACTTGCTTC  5040
5041  CATAAAAATGATAAGCAGTATGTTTAAGTGATCTTTATGATAAGATTATTGATATATTTG  5100
5101  GCCTTGTTTCTCCCCATGGTACTCAGTTGTCTCTGGCTTCTGTATCCCATGGAATGGCAG  5160
5161  TGAGTAACCAAGACAAGCTGTGGCCTTCTTATACGTTGATGAATCCTCTGGCACTTAAAT  5220
5221  CTGTCTTTCTTTAATTATTTTTTCAGCTGGTAAGCGATTCTGGTTATAATTTTAAAGCT  5280
5281  GTCAGGAGATGGACTACGCAGAGAAAGTTGGGATATGCTCTTATTGACTGTGACATGGTA  5340
5341  ATTTTGTCGAAGAACCTGAATTTGAAGATTCTCTTGTTAATATTACGCATGTAGTCCAAT  5400
5401  TTATTTATGTTAACTTAGTCTGTGCCCTCTGCAGATATTTGTTCCCATCCACAGGGGTG   5460
5461  TGCATTGGACCTTGGCAGTAATTAACAACAGGGAAAGCAAGCTCTTGTATCTTGATTCAC  5520
5521  TGAATGGAGTTGATCCTATGATTCTGAATGCTCTGGTATGATTTAATTTCTAACTCTTAT  5580
5581  TCGCTTTATTTAGTCTATTAATAACTGACATGTTGGATGCATTAAAAGATATTAGATGCT  5640
5641  GATAAATCTTTATCATCATTTCTTGATTCTGAAATCTGTTTGGAGACATTATGGAGATGC  5700
5701  CAGAAGCTGTTATTGCTTTTTAAATCGGACACTACTGTGAAAGTGTTCTAACCATATATA  5760
5761  CTAGTCGTTATAGCTAATGCCAGATCTGATATTCTGCTTCAGGCAAAATACATGGGTGAT  5820
5821  GAAGCAAATGAAAAAGTGGAAAAAGATTGATGCTAATTCGTGGGACATGGAATTTGTG    5880
5881  GAAGACCTTCCCCAACAAAAGAATGGGTATGTAACTATGCTTGAACTTGCTATGATCCAT  5940
5941  GATCATGTGAAAGGAACTATCTTGTTAAAGAGATAACCTCTGTAGAATCAGATACTTGTC  6000
6001  TTCTGATGTGGGAATATGGGTTTTTAAGACAAAGGATAGATCTGGTTTGAGATTGATTAG  6060
6061  GAGAAATTCACCTGATATAAATTTTGATAATGGAATCAACAAGGGTATAACTTAACTGTT  6120
6121  CTTATGCTCTTTAGCACTCTGGTTAAGCTCTCTGCTAACTCTATATTGTTTCTTTGTTGC  6180
6181  AATCTTTTATATTCTCAGGTATGACTGTGGAATGTTTATGCTTAAGTACATCGATTTTTT  6240
6241  CAGCAGAGGCCTGGGGCTATGTTTCAGCCAGGTAAGCTATCAGAATCCAAATCTCTGAAT  6300
6301  GCCTCAAGAAACTGTAGTTGAGAATAAAAACTGGTTGTCTTGAAACAATATGGAATTAGT  6360
6361  ATATCCCCCTAGCAGTTTATGTAACTTGTAGGATTTAGGCATTTAGCGTAATAACATTGT  6420
6421  ATTACTTTGCAGGAACACATGCCATACTTCCGACTCAGAACAGCTAAAGAGATTCTGAGG  6480
6481  CTACGAGCTGATTGAAGTTGCTTGTGCTAATGTTTTTTCGGCTATTAGGAATACTATTTT  6540
6541  TGGTTGCCATTGTTGATTTGTTCAAACTTTAAATCCCACTCCTTTTAGGCAGTGAAGCAC  6600
6601  TCGGCTTTAAAAGCAGAGGTAAAAACTGAGTCAAGCCCAGAGCTCTTAGCTCGTTCCGTT  6660
6661  ATTGTATTTTTTTCCTTCTTCTTGTTTTAAAATGTAGATGAAGCGTTTTGGATCTCTATG  6720
6721  TTGGTTAGTCTAGCTGAAGATATATGAGATGTTGAAAACCTTATTTATTTCTCTCCGGTC  6780
6781  TTGACCAGTGCGAACGCAATTTAAAGTTTCCATCTAGTATCGGTTCGATATATTTTCCTC  6840
6841  TGTTCAATAGCCAAAATTCCATGAATAATCTCTTGAAAGCAAATGTTTTCGATATACAAA  6900
6901  TGTTCTGCACAATTTCCCCAATACATACACGAATATGTTACAAATATACAACAAACTGCT  6960
6961  GTTTGTGAGTACAAACCCACTCCCAAAAACAAAAACAAATTCCCCAATTCATAAAACACGAGAG  7020
7021  ACATATTAAAACCCACTCCCAAAAAACATGAAATAATGTTAAAACAATCACAAGACATATGA  7080
7081  GAAGGAAGACTTGTGTGTATCTCCTAACAAAAACTGACTGGAAGGCAAACTAACTTCCAC  7140
7141  TGCCTTTCCTAGCGCGGAACTCTCTTCCGGCTAAGTATCTCCTGTTCTTTCAGACGGTGT  7200
7201  TGGAACCGAGCAAGACGGGCTTGAAGACTTACAAGACCAGCTGCTTTACGGGACAACACA  7260
7261  AAGCTCAGCTGTGTAACATAGTTGTCAATCATGCTCCCTGGCCGATCCACCTTCGCTAGT  7320
7321  AATTTCATTTCCTACAAAAAAAACATGAAATAATGTTAAAACAATCACAAGACATATGA   7380
7381  GCCATAACCTCGTGAACTATTTCCATTGTATCCTCGATCTCTTTTCTGTGTGCTGTAATT  7440
7441  AAGGTCTCTTCTTCCTGCCAGAGTTTAAACAAAATAATTACCATATTACAGGTTTTCTAA  7500
7501  GGTTATTCGTGAGCGATATTCATAAAATTCCCTCACGCTCATAGCATAATTTAGAAGTAT  7560
7561  AGAAGGGTCAAATGGCTCTTTACCTCAAGCAATGCATCAATGTTTTCATCAAGAGAAGGC  7620
7621  TCCGTTGTTTCATACTGCCTTGAAGATGTATCGCCTTGTGTTCTGACTGCTAGCCATATTT  7680
7681  TGTTGTCTAGAATTTGTCATGGCAGGGACATCAGTCTTGAGAATAAGATGAGTGAATCCT  7740
7741  TTGACTAGTGGAGCCGCCAAAAGAAGATTTTAAAATGTTAAGCATAAATCATATTCCTTA  7800
7801  AATGTTAAGTGAATCCTTTGACTAGTATAGTATAGTGTCTGGTTTTTCATTAGACTTTCT  7860
7861  GAGATGAGAGGTATTTCTATTAAAACTTAAGTTGAAGGTTTTAAAATGAATCAGCCAAAA  7920
7921  CTGCAGGGTTTGTTTCATTAAAATCCCAAAATTGTTCGTATACATCATATTACCCACTG   7980
```

Fig. 2C

```
7981  AGGACTCTGCTCTTTGTGGAAATGCTAAATTAGCCCCAAACCTTTTTCTAAGTCCCACTT  8040
8041  TGAATTCTAATAAGAACGAACAGATCGCGGGAAATCCAAAATGATTTGAAACCTTTTCAC  8100
8101  CTGAATTTCTGTGAAATCCAAAATTCTCTCTCTATCAGTAGAGAATCGCCATGGATGAAG  8160
8161  AGCTTCTGCTCACTAGAATCCTTGCAGGAATCGAAGGAGGAGACGATGAATCTGACTATC  8220
8221  ATGAACTCGTCACGGATCTCAAATCTCTACTTGATACAGACGATGATGAAATTCTCAATC  8280
8281  GATTCTACGGTAGTCTCTCCTCAATGGCTTCTTCGTTTCTCCGCTGTATCTCCGCCGCCA  8340
8341  TGGATTCTCCGGTTGAATCAGGCCGTCTTGCTATTTTAGCCTCCGACGCTTATCTCAGTC  8400
8401  TGCTTCTTTCCACGAATTGCCCCGTTTTCACTTTCTTCTCTCCGATTGCGTTTCTTTCTC  8460
8461  TACTTGGCTCAATTCGCCGCTACCTCAAACGCCGTGATGATTCCGCCGGTCAAGGGAGTA  8520
8521  ATTCGCAGCGAGAGAAAGGGAATAAGAAGAAGAGAGGACGTGGTAAGAGGAATTTAGGGT  8580
8581  ATGAAGATGGGGAAGAGACTGAAGAAGGTGGATTTGATGCGAAATTGATGTTTATAGTGT  8640
8641  TAGAGAAGCTTGGCTCGGTTCTGAGTTTTGTTCATTTAGATAGATTTCCTGATAGTTTGA  8700
8701  AATCTTTGGTACAAACTGTGAGTGAGATTCCTTTATTGGCGTTGGAGCACTCTGGAGTTT  8760
8761  TGAATTATGATCGATTGATGGAAATGTGTGGGAAGATTCTGGGAGGAGTGTTGAATTCTG  8820
8821  ACCATGAGATATGGCACTCACTGCTGCTGAGATTTCAAAGTCTTTGACACCGTTGCTTC  8880
8881  TTATGGGGAAACATCAAGCGAGAAGTTTTGCGTTGGGATTTGTGTCAAGGAAATTGATGA  8940
8941  GTTTGGCTAAAGATAACCCTGAATTGAAAAAAGTTGTGTCTAATTTGCCTAAGTTTCTGG  9000
9001  TTCATAAGGCACCTGAGAAGGCCGAGCCGCGTGGATTTGCAGTGGAGGCGGTACTGGAGA  9060
9061  TTGTAAAGGCAATGGAGGTTGAGGGCCAATCAGAGTTTGTTGATTTTGTAATGAAGATGT  9120
9121  GTCAAGGGAAGTCTAATTTTAGAGTATTAGCTGTTGATATTATACCTCTGTTGATAAGCT  9180
9181  CATTAGGAAACCCTCTAGGAGATATTAGTTCAGAGAATGGGTTGAAAGATTCGTGGGGCT  9240
9241  TGGGTTGTATTGATGCTTTAGTTCAGCGGTGTTCAGACACGAGCGCTTTGATTAGAGCTC  9300
9301  GAGCTTTGTCCAACTTGGCTCAAGTTGTGGAGTTCTTGTCTGGTGATGAAAGGAGTAGGT  9360
9361  CGATCGTGAAACAAGCCCTTGGGTTTAACGGTGAGACTTCAGAGGGAAAAGGTGCAGTAA  9420
9421  CTGACCTTTTGAAGAAAAGATGTGTGGATGAGAAGGCGGCTGTAAGGAGAGCAGCTCTTC  9480
9481  TTCTGGTGACAAAATTGACATCGCTTATGGGTGGTTGCTTTGATGGTAGTATCCTAAAGA  9540
9541  CAATGGGTACATCTTGTTCTGATCCGCTAATAAGTATAAGAAAGGCTGCAGTTTCAGCTA  9600
9601  TTTCCGAGGTATGTTTTCTGTAACTCAGTTTCTTCTTTCTCATTTACCCGATGGTAATAT  9660
9661  GTGTAGAGTTAGTATAATTTATACGGGTTTGCTTTGACCTTAATTAGCTCAAAGTTAAAG  9720
9721  AGACCAAATGTGCAAGCCAAAAATGTTTTTAGATGAATGAATGGGAAATTACATAGCAAC  9780
9781  TGCTTCCGTCGGTTTCATACTAAAATCAGATAATCTTTATACTTTAACTTATCCCTGAAT  9840
9841  ATAGGTCAGGCACTCAGGCTAATGACTTGTTATCATATTTCTCTGATGATGCAAGTTCAT  9900
9901  TGTCTTCTGTTCACTGTAGGCATTCAGAATATGTACAGATGAAATTGTGACCACTGAATG  9960
9961  GTTACAATTCTGTTCCTCGGATGATCATGGACAATGAAACTAGCATCCAAGAAGAATGCGA  10020
10021 GAATGTCTTTCATGAATTAGTTCTGGAGAGAATATTACGAGCTGGAAATGTGCTTTCTCC  10080
10081 AGACAGTGCTTCTCTCCCTAACAACCGGAACACTACTTCAAAAGATCTAGACAGAGACAT  10140
10141 TGAAGCCTTGTTTCCAGAAGGAGTTTTGGTTCTCTTAAGGGAGCTTTGCAACAGTGAGGT  10200
10201 TTCTCCTTGGGTTACGAAAATATGTGGAAGTTTGGGAAAGAAGAAGCGACTAAAACCAAG  10260
10261 AGTTGCCCTTGCGCTTCAGTGTATCATAAAGGAATCTGAATCACTGTGGTTGAGTCGTTC  10320
10321 AATGCCAATAAATAGATGGACAGCTCCTGCTGGTGCTTGGTTCCTTCTATCAGAGGTTTC  10380
10381 AGTTTATCTTTCAAAGTCTGTCGAATGGAATTTCTTCACCATCATTGGCAGTTGCTTGA  10440
10441 CAAGAATGACGTACAAGGTTTGTCAGAATTCTGTTTAT  10478
```

```
  1 GCCGCCTCGGCTTTGAGCAGCTCGCCGATGTCCTCCCACGGTTCGGGCCCCGGAAGGAGG    60
 61 ATGAACCTTTTGTTCCTTTTACGGATGAGGATGAGGATAGTGTTGATCATGCTCTTGGTG   120
121 GCCGTAACAGACGTGAAAGGCTAGTGGTACATGAATCATCAAATATTGTCATAACAAGAG   180
181 AGACCTTGCAGTGCTTGAACGAAACGGAGTGNCTAAATGATGAGGTCATAAATTTGTATC   240
241 TTGAGCTGCTGAAAGAGAGGGAACTGAGAGAACCTAACAAGTTTTTGAAATGCCACTTCT   300
301 TCAATACCTTTTTCTACAAAAAGCTCATTACTGGTGGGTATGATTATAAGTCTGTCAGAA   360
361 GATGGACAACTAAAAGGAAGTTAGGTTACAGCCTACTTGAATGTGATAAGATCTTTGTTC   420
421 CTATACACAAGGAAGTGCATTGGTGTTTAGCAGTCATAAACATAAGGGACAAAAAGTTTC   480
481 AATTTCTGGATTCACTTGGCAGCATGGACATGAAGGCATTGAGAACTTTAGCAAGGTATC   540
541 TTGTAGATGAGGTGAAAGATAAGAGTGGCCAACATATTGATGCTCTTTCATGGNAGCAGG   600
601 AGGGTGTAAAAAACCTTCCTTTGCAAGAGAA   631
```

Fig. 4B

```
  1 GCACTTCATGTATTCAGTACTTTCTTCTATCCTAAATTAAAGTCTGGGGGTTACCAAGCA    60
 61 GTGAAACGANTGGACCAAAGGGGTAAATCTCTTTGAACAAGAAATTATTCTGGTGCCTAT   120
121 TCATCGGAAGGTACATTGGAGCCTGGTGGTGATTGACCTAAGAAAAAAGTGTCTTAAATA   180
181 TCTGGATTCTATGGGACAAAAGGGCCACAGGATCTGTGAGATTCTCCTTCAGTATTTACA   240
241 GGATGAAAGTAAGACCAAAAGAAATAGTGATCTGAATCTTTTAGAGTGGACCCATCACAG   300
301 CATGAAACCACACGAGATTCCTCAACAGCTGAATGGGAGTGATTGTGGAATGTTTACTTG   360
361 TAAATATGCAGATTATATTTCTAGGGACAAACCTATCACATTTACTCAGCACCAGATGCC   420
421 TCTCTTCCGGAAGAAGATGGTGTGGGAAATCCTTCATCAGCAGTTGCTGTGAGAAAACTT   480
481 TGCCTGGTCCTCTAGCTGCTGGTGGTTCTTTCACAGACATTTCCATATANCCTCATGCAT   540
541 GTGGGTTAAAAAGTCCCTGCATCACTTCTGTTCTCACAGGTACTGAGCTGTCAAA   595
```

ARABIDOPSIS ESD4 GENE AND METHOD TO CONTROL FLOWERING TIME

This is a 371 of PCT/GB98/01714, filed Jun. 12, 1998, which claims priority from GB 9712415.0, filed Jun. 13, 1997.

This invention relates to the genetic control of flowering in plants and the cloning and expression of genes involved therein. More particularly, the invention relates to the cloning and expression of the EARLY SHORT DAYS 4 gene of *Arabidopsis thaliana*, and homologues from other species, and manipulation and use of these genes in plants.

Efficient flowering in plants is important, particularly when the intended product is the flower or the seed produced therefrom. One aspect of this is the timing of flowering: advancing or retarding the onset of flowering can be useful to farmers and seed producers. An understanding of the genetic mechanisms which influence flowering provides a means for altering the flowering characteristics of the target plant. Species for which flowering is important to crop production are numerous, essentially all crops which are grown from seed, with important examples being the cereals, rice and maize, probably the most agronomically important in warmer climatic zones, and wheat, barley, oats and rye in more temperate climates. Important seed products are oil seed rape and canola, sugar beet, maize, sunflower, soybean and sorghum. Many crops which are harvested for their roots or leaves are, of course, grown annually from seed and the production of seed of any kind is very dependent upon the ability of the plant to flower, to be pollinated and to set seed. Delaying flowering is important in increasing the yield of plants from which the roots or leaves are harvested. In horticulture, control of the timing of flowering is important. Horticultural plants whose flowering may be controlled include lettuce, endive, spinach and vegetable brassicas including cabbage, broccoli and cauliflower, and carnations and geraniums.

*Arabidopsis thaliana* is a facultative long day plant, flowering early under long days and late under short days. Because it has a small, well-characterized genome, is relatively easily transformed and regenerated and has a rapid growing cycle, Arabidopsis is an ideal model plant in which to study flowering and its control.

BRIEF DESCRIPTION OF THE INVENTION

The present inventors have discovered that one of the genes that regulates flowering time in Arabidopsis is a gene termed the EARLY SHORT DAYS 4 or ESD4 gene. The present inventors have found that plants carrying a recessive mutation affecting the ESD4 gene flower earlier than their wild-types under long and short days. The ESD4 gene has now been cloned and sequenced and the inventors have demonstrated that the mutation is a deletion removing part of the gene. This provides indication that reducing or abolishing ESD4 function accelerates flowering, and therefore that the ESD4 gene likely encodes a repressor of flowering.

DETAILED DESCRIPTION OF THE INVENTION

According to a first aspect of the present invention there is provided a nucleic acid molecule including a nucleotide sequence encoding a polypentide with ESD4 function. Those skilled in the art will appreciate that "ESD4 function" may be used to refer to the ability to influence the timing, of flowering phenotypically when its expression is reduced like the ESD4 gene of *Arabidopsis thaliana*. esd4 mutants exhibit early flowering under long and short days, the timing of flowering being substantially unaffected by vernalisation.

The present invention provides a nucleic acid isolate encoding a polypeptide including the amino acid sequence shown in FIG. 1, which may include the coding sequence shown in FIG. 1 which is that of the ESD4 gene of *Arabidopsis thaliana*. FIG. 2 shows a genomic sequence including nucleotides encoding the polypeptide for which the amino acid sequence is shown in FIG. 1.

Nucleic acid according to the present invention may have the sequence of an ESD4 gene of *Arabidopsis thaliana*, or be a mutant, variant, derivative or allele or a homologue of the sequence provided. Preferred mutants, variants, derivatives and alleles are those which encode a protein which retains a functional characteristic of the protein encoded by the wild-type gene, especially the ability to affect a physical characteristic of a plant, such as a flowering characteristic, especially the ability to repress flowering as discussed herein.

A mutant, variant, derivative or allele in accordance with the present invention may have the ability to affect a physical characteristic of a plant, particularly a flowering characteristic. In various embodiments a mutant, variant, derivative or allele represses flowering compared with wild-type on expression in a plant, e.g. compared with the effect obtained using a gene sequence encoding the polypeptide of FIG. 1. "Repression" of flowering delays, retards, inhibits or slows it down. In other embodiments, a mutant, variant, derivative or allele promotes flowering compared with wild-type on expression in a plant, e.g. compared with the effect obtained using a gene sequence encoding the polypeptide of FIG. 1. "Promotion" of flowering advances, accelerates or brings it forward. Comparison of effect on flowering or other characteristic may be performed in *Arabidopsis thaliana*, although nucleic acid according to the present invention may be used in the production of a wide variety of plants and for influencing a characteristic thereof.

As discussed further below, over-expression of nucleic acid according to the present invention may delay flowering while under expression may promote flowering in a transgenic plant.

Changes to a sequence, to produce a mutant, variant or derivative, may be by one or more of addition, insertion, deletion or substitution of one or more nucleotides in the nucleic acid, leading to the addition, insertion, deletion or substitution of one or more amino acids in the encoded polypeptide. Of course, changes to the nucleic acid which make no difference to the encoded amino acid sequence are included.

A preferred nucleic acid sequence for an ESD4 gene including a coding sequence according to the present invention is shown in FIG. 1, along with the predicted amino acid sequence of a polypeptide according to the present invention which has ESD4 function.

A mutant, allele, variant or derivative amino acid sequence in accordance with the present invention may include within the sequence shown in FIG. 1, a single amino acid change with respect to the sequence shown in FIG. 1, or 2, 3, 4, 5, 6, 7, 8, or 9 changes, about 10, 15, 20, 30, 40 or 50 changes, or greater than about 50, 60, 70, 80 or 90 changes. In addition to one or more changes within the amino acid sequence shown in FIG. 1, a mutant, allele, variant or derivative amino acid sequence may include additional amino acids at the C-terminus and/or N-terminus.

A sequence related to a sequence specifically disclosed herein shares homology with that sequence. Homology may be at the nucleotide sequence and/or amino acid sequence level. Preferably, the nucleic acid and/or amino acid sequence shares homology with the coding sequence or the sequence encoded by the nucleotide sequence of FIG. 1, preferably at least about 50%, or 60%, or 70%, or 80% homology, most preferably at least about 90%, 95%, 96%, 97%, 98% or 99% homology.

As is well-understood, homology at the amino acid level is generally in terms of amino acid similarity or identity. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Similarity may be as defined and determined by the TBLASTN program, of Altschul et al. (1990) J. Mol. Biol. 215: 403–10, which is in standard use in the art, or, and this may be preferred, the standard program BestFit, which is part of the Wisconsin Package, Version 8, September 1994, (Genetics Computer Group, 575 Science Drive, Madison, Wisconsin, USA, Wisconsin 53711). BestFit makes an optimal alignment of the best segment of similarity between two sequences. Optimal alignments are found by inserting gaps to maximize the number of matches using the local homology algorithm of Smith and Waterman (Adv. Appl. Math. (1981) 2: 482–489).

Homology may be over the full-length of the relevant sequence shown herein, or may more preferably be over a contiguous sequence of about or greater than about 20, 25, 30, 33, 40, 50, 67, 133, 167, 200, 233, 267, 300, 333 or more amino acids or codons, compared with the relevant amino acid sequence or nucleotide sequence as the case may be.

Also provided by an aspect of the present invention is nucleic acid including or consisting essentially of a sequence of nucleotides complementary to a nucleotide sequence hybridisable with any encoding sequence provided herein. Another way of looking at this would be for nucleic acid according to this aspect to be hybridisable with a nucleotide sequence complementary to any encoding sequence provided herein. Of course, DNA is generally double-stranded and blotting techniques such as Southern hybridisation are often performed following separation of the strands without a distinction being drawn between which of the strands is hybridising. Preferably the hybridisable nucleic acid or its complement encode a product able to influence a physical characteristic of a plant, particularly a flowering characteristic such as the timing of flowering. Preferred conditions for hybridisation are familiar to those skilled in the art, but are generally stringent enough for there to be positive hybridisation between the sequences of interest to the exclusion of other sequences.

The nucleic acid, which may contain for example DNA encoding the amino acid sequence of FIG. 1, as genomic (see e.g. FIG. 2) or cDNA, may be in the form of a recombinant and preferably replicable vector, for example a plasmid, cosmid, phage or Agrobacterium binary vector. The nucleic acid may be under the control of an appropriate promoter or other regulatory elements for expression in a host cell such as a microbial, e.g. bacterial, or plant cell. In the case of genomic DNA, this may contain its own promoter or other regulatory elements and in the case of cDNA this may be under the control of an appropriate promoter or other regulatory elements for expression in the host cell.

A vector including nucleic acid according to the present invention need not include a promoter or other regulatory sequence, particularly if the vector is to be used to introduce the nucleic acid into cells for recombination into the genome.

Those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual*: 2nd edition, Sambrook et al, 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology, Second Edition*, Ausubel et al. eds., John Wiley & Sons, 1992. The disclosures of Sambrook et al. and Ausubel et al. are incorporated herein by reference. Specific procedures and vectors previously used with wide success upon plants are described by Bevan (Nucl. Acids Res. 12, 8711–8721 (1984)) and Guerineau and Mullineaux (1993) (Plant transformation and expression vectors. In: Plant Molecular Biology Labfax (Croy RRD ed) Oxford, BIOS Scientific Publishers, pp 121–148).

Selectable genetic markers may be used consisting of chimaeric genes that confer selectable phenotypes such as resistance to antibiotics such as kanamycin, hygromycin, phosphinotricin, chlorsulfuron, methotrexate, gentamycin, spectinomycin, imidazolinones and glyphosate.

Nucleic acid molecules and vectors according to the present invention may be provided isolated and/or purified from their natural environment, in substantially pure or homogeneous form, or free or substantially free of nucleic acid or genes of the species of interest or origin other than the sequence encoding a polypeptide with the required function. Nucleic acid according to the present invention may include cDNA, RNA, genomic DNA and may be wholly or partially synthetic. The term "isolate" encompasses all these possibilities. Where a DNA sequence is specified, e.g. with reference to a figure, unless context requires otherwise the RNA equivalent, with U substituted for T where it occurs, is encompassed.

When introducing a chosen gene construct into a cell, certain considerations must be taken into account, well known to those skilled in the art. The nucleic acid to be inserted should be assembled within a construct which contains effective regulatory elements which will drive transcription. There must be available a method of transporting the construct into the cell. Once the construct is within the cell membrane, integration into the endogenous chromosomal material either will or will not occur. Finally, as far as plants are concerned the target cell type must be such that cells can be regenerated into whole plants.

Plants transformed with the DNA segment containing the sequence may be produced by standard techniques which are already known for the genetic manipulation of plants. DNA can be transformed into plant cells using any suitable technology, such as a disarmed Ti-plasmid vector carried by Agrobacterium exploiting its natural gene transfer ability (EP-A-270355, EP-A-0116718, NAR 12(22) 8711–87215 1984), particle or microprojectile bombardment (US 5100792, EP-A-444882, EP-A-434616) microinjection (WO 92/09696, WO 94/00583, EP 331083, EP 175966, Green et al. (1987) Plant *Tissue and Cell Culture*, Academic Press), electroporation (EP 290395, WO 8706614 Gelvin Debeyser—see attached) other forms of direct DNA uptake (DE 4005152, WO 9012096, US 4684611), liposome mediated DNA uptake (e.g. Freeman et al.

*Plant Cell Physiol.* 29: 1353 (1984)) or the vortexing method (e.g. Kindle, *PNAS U.S.A.* 87: 1228 (1990d) Physical methods for the transformation of plant cells are reviewed in Oard, 1991, *Biotech. Adv.* 9: 1–11.

Agrobacterium transformation is widely used by those skilled in the art to transform dicotyledonous species. Recently, there has been substantial progress towards the routine production of stable, fertile transgenic plants in almost all economically relevant monocot plants (criyama, et al. (1988) *Bio/Technology* 6, 1072–1074; Zhang, et al. (1988) Plant Cell Rep. 7, 379–384; Zhang, et al. (1988) *Theor Appl Genet* 76, 835–840; Shimamoto, et al. (1989) *Nature* 338, 274–276; Datta, et al. (1990) *Bio/Technology* 8, 736–740; Christou, et al. (1991) *Bio/Technology* 9, 957–962; Peng, et al. (1991) International Rice Research Institute, Manila, Philippines 563–574; Cao, et al. (1992) *Plant Cell Rep.* 11, 585–591; Li, et al. (1993) *Plant Cell Rep.* 12, 250–255; Rathore, et al. (1993) *Plant Molecular Biology* 21, 871–884; Fromm, et al. (1990) *Bio/Technology* 8, 833–839; Gordon-Kamm, et al. (1990). *Plant Cell* 2, 603–618; D'Halluin, et al. (1992) *Plant Cell* 4, 1495–1505; Walters, et al. (1992) *Plant Molecular Biology* 18, 189–200; Koziel, et al. (1993) *Biotechnology* 11, 194–200; Vasil, I. K. (1994) *Plant Molecular Biology* 25, 925–937; Weeks, et al. (1993) *Plant Physiology* 102, 1077–1084; Somers, et al. (1992), *Bio/Technology* 10, 1589–1594; WO92/14828). In particular, Agrobacterium mediated transformation is now emerging also as an highly efficient alternative transformation method in monocots (Hiei et al. (1994) *The Plant Journal* 6, 271–282)

The generation of fertile transgenic plants has been achieved in the cereals rice, maize, wheat, oat, and barley (reviewed in Shimamoto, K. (1994) *Current Opinion in Biotechnology* 5, 158–162.; Vasil, et al. (1992) *Bio/Technology* 10, 667–674; Vain et al., 1995, *Biotechnology Advances* 13 (4): 653–671; Vasil, 1996, *Nature Biotechnology* 14 page 702).

Microprojectile bombardment, electroporation and direct DNA uptake are preferred where Agrobacterium is inefficient or ineffective. Alternatively, a combination of different techniques may be employed to enhance the efficiency of the transformation process, eg bombardment with Agrobacterium coated microparticles (EP-A-486234) or microprojectile bombardment to induce wounding followed by co-cultivation with Agrobacterium (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewd in Vasil et al., *Cell Culture and Somatic Cell Genetics of Plants, Vol I, II and III, Laboratory Procedures and Their Applications*, Academic Press, 1984, and Weissbach and Weissbach, Methods for Plant *Molecular Biology*, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

A ESD4 gene and modified versions thereof (alleles, mutants, variants and derivatives thereof), and other nucleic acid provided herein, including species homologues, may be used to affect a physical characteristic, such as a flowering characteristic which may include timing of flowering, in plants. For this purpose nucleic acid such as a vector as described herein may be used for the production of a transgenic plant. Such a plant may possess an altered flowering phenotype, particular in terms of timing of flowering, compared with wild-type (that is to say a plant that is wild-type for ESD4 or the relevant homologue thereof).

The invention further encompasses a host cell transformed with nucleic acid or a vector according tot he present invention, especially a plant or a microbial cell. Thus, a host cell, such as a plant cell, including heterologous nucleic acid according to the present invention is provided. Within the cell, the nucleic acid may be incorporated within the chromosome. There may be more than one heterologous nucleotide sequence per haploid genome.

Also according to the invention there is provided a plant cell having incorporated into its genome nucleic acid, particularly heterologous nucleic acid, as provided by the present invention, under operative control of a regulatory sequence for control of expression. The coding sequence may be operably linked to one or more regulatory sequences which may be heterologous or foreign to the gene, such as not naturally associated with the gene for its expression. The nucleic acid according to the invention may be placed under the control of an externally inducible gene promoter to place expression under the control of the user.

A suitable inducible promoter is the GST-II-27 gene promoter which has been shown to be induced by certain chemical compounds which can be applied to growing plants. The promoter is functional in both monocotyledons and dicotyledons. It can therefore be used to control gene expression in a variety of genetically modified plants, including field crops such as canola, sunflower, tobacco, sugarbeet, cotton; cereals such as wheat, barley, rice, maize, sorghum; fruit such as tomatoes, mangoes, peaches, apples, pears, strawberries, bananas, and melons; and vegetables such as carrot, lettuce, cabbage and onion. The GST-II-27 promoter is also suitable for use in a variety of tissues, including roots, leaves, stems and reproductive tissues. Another example of an inducible promoter is the ethanol inducible gene switch disclosed in Caddick et al (1998) Nature Biotechnology 16: 177–180. Many other examples are known to those skilled in the art.

Other suitable promoters may include the Cauliflower Mosaic Virus 35S (CaMV 35S) gene promoter that is expressed at a high level in virtually all plant tissues (Benfey et al, (1990a) EMBO J 9: 1677–1684); the cauliflower meri 5 promoter that is expressed in the vegetative apical meristem as well as several well localised positions in the plant body, eg inner phloem, flower primordia, branching points in root and shoot (Medford, J. I. (1992). *Plant Cell* 4, 1029–1039; Medford et al, (1991) *Plant Cell* 3, 359–370) and the *Arabidorsis thaliana* LEAFY promoter that is expressed very early in flower development (Weigel et al, (1992) Cell 69, 843–859).

A further aspect of the present invention provides a method of making such a plant cell involving introduction of nucleic acid or a suitable vector including the sequence of nucleotides into a plant cell and causing or allowing recombination between the vector and the plant cell genome to introduce the sequence of nucleotides into the genome. The invention extends to plant cells containing nucleic acid according to the invention as a result of introduction of the nucleic acid into an ancestor cell.

The term "heterologous" may be used to indicate that the gene/sequence of nucleotides in question have been introduced into said cells of the plant or an ancestor thereof, using genetic engineering, ie by human intervention. A transgenic plant cell, i.e. transgenic for the nucleic acid in question, may be provided. The transgene may be on an extra-genomic vector or incorporated, preferably stably, into the genome. A heterologous gene may replace an endogenous equivalent gene; ie one which normally performs the same or a similar function, or the inserted sequence may be additional to the endogenous gene or other sequence. An advantage of introduction of a heterologous gene is the ability to place expression of a sequence under the control of a promoter of choice, in order to be able to influence expression according to preference. Furthermore, mutants, variants and derivatives of the wild-type gene, e.g. with higher or lower activity than wild-type, may be used in place of the endogenous gene. Nucleic acid heterologous, or exogenous or foreign, to a plant cell may be non-naturally occuring in cells of that type, variety or species. Thus, nucleic acid may include a coding sequence of or derived from a particular type of plant cell or species or variety of plant, placed within the context of a plant cell of a different type or species or variety of plant. A further possibility is for a nucleic acid sequence to be placed within a cell in which it or a homologue is found naturally, but wherein the nucleic acid sequence is linked and/or adjacent to nucleic acid which does not occur naturally within the cell, or cells of that type or species or variety of plant, such as operably linked to one or more regulatory sequences, such as a promoter sequence, for control of expression. A sequence within a plant or other host cell may be identifiably heterologous, exogenous or foreign.

Plants which include a plant cell according to the invention are also provided, along with any part or propagule thereof, seed, selfed or hybrid progeny and descendants. A plant according to the present invention may be one which does not breed true in one or more properties. Plant varieties may be excluded, particularly registrable plant varieties according to Plant Breeders' Rights. It is noted that a plant need not be considered a "plant variety" simply because it contains stably within its genome a transgene, introduced into a cell of the plant or an ancestor thereof.

In addition to a plant, the present invention provides any clone of such a plant, seed, selfed or hybrid progeny and descendants, and any part of any of these, such as cuttings, seed. The invention provides any plant propagule, that is any part which may be used in reproduction or propagation, sexual or asexual, including cuttings, seed and so on. Also encompassed by the invention is a plant which is a sexually or asexually propagated off-spring, clone or descendant of such a plant, or any part or propagule of said plant, off-spring, clone or descendant.

The invention further provides a method of influencing or affecting a physical e.g. flowering characteristic such as the timing of flowering of a plant, including causing or allowing expression of a heterologous nucleic acid sequence as discussed within cells of the plant.

The invention further provides a method of including expression from nucleic acid encoding the amino acid sequence of FIG. 1, or a mutant, variant, allele or derivative of the sequence, within cells of a plant (thereby producing the encoded polypeptide), following an earlier step of introduction of the nucleic acid into a cell of the plant or an ancestor thereof. Such a method may influence or affect a flowering characteristic of the plant, such as the timing of flowering. This may be used in combination with any other gene, such as transgenes involved in flowering or other phenotypic trait or desirable property.

The present invention also encompasses the expression product of any of the nucleic acid sequences disclosed and methods of making the expression product by expression from encoding nucleic acid therefore under suitable conditions, which may be in suitable host cells. Following expression, the product may be isolated from the expression system and may be used as desired, for instance in formulation of a composition including at least one additional component.

A further aspect of the present invention provides a method of identifying and cloning ESD4 homologues from plant species other than *Arabidopsis thaliana* which method employs a nucleotide sequence derived from that shown in FIG. 1. Sequences derived from these may themselves be used in identifying and in cloning other sequences. The nucleotide sequence information provided herein, or any part thereof, may be used in a data-base search to find homologous sequences, expression products of which can be tested for ability to influence a flowering characteristic. These may have ESD4 function or the ability to repress flowering. Alternatively, nucleic acid libraries may be screened using techniques well known to those skilled in the art and homologous sequences thereby identified then tested.

Target or candidate nucleic acid may, for example, comprise genomic DNA, cDNA or RNA (or a mixture of any of these preferably as a library) obtainable from an organism known to contain or suspected of containing such nucleic acid, either monocotyledonous or dicotyledonous. Prior to any PCR that is to be performed, the complexity of a nucleic acid library may be reduced by creating a cDNA library for example using RT-PCR or by using the phenol emulsion reassociation technique (Clarke et al. (1992) NAR 20, 1289–1292) on a genomic library. Successful hybridisation may be identified and target/candidate nucleic acid isolated for further investigation and/or use.

Hybridisation of nucleic acid molecule to a ESD4 gene or homologue may be determined or identified indirectly, e.g using a nucleic acid amplification reaction, particularly the polymerase chain reaction (PCR). PCR requires theuse of two primers to specifically amplify target nucleic acid, so preferably two nucleic acid molecules with sequences characteristic of ESD4 are employed. However, if RACE is used, only one such primer may be needed. Hybridisation may be also be determined (optionally in conjunction with an amplification technique such as PCR) by probing with nucleic acid and identifying positive hybridisation under suitably stringent conditions (in accordance with known techniques). For probing, preferred conditions are those which are stringent enough for there to be a simple pattern with a small number of hybridisations identified as positive which can be investigated further. It is well known in the art to increase stringency of hybridisation gradually until only a few positive clones remain.

Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include examination of restriction fragment length polymorphisms, amplification using PCR, RNAase cleavage and allele specific oligonucleotide probing.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined. DNA for probing may be prepared from RNA preparations from cells by techniques such as reverse-transcriptase- PRC.

Preliminary experiments may be performed by hybridising under low stringency conditions various probes to Southern blots of DNA digested with restriction enzymes. For probing, preferred conditions are those which are stringent enough for there to be a simple pattern with a small number of hybridisations identified as positive which can be investigated further. It is well known in the art to increase stringency of hybridisation gradually until only a few positive clones remain. Suitable conditions would be achieved when a large number of hybridising fragments were obtained while the background hybridisation was low. Using these conditions nucleic acid libraries, e.g. cDNA libraries representative of expressed sequences, may be searched. Those skilled in the art are well able to employ suitable conditions of the desired stringency for selective hybridisation, taking into account factors such as oligonucleotide length and base composition, temperature and so on.

For instance, screening may initially be carried out under conditions, which comprise a temperature of about 37° C. or more, a formamide concentration of less than about 50%, and a moderate to low salt (e.g. Standard Saline Citrate ('SSC')=0.15 M sodium chloride; 0.15 M sodium citrate; pH 7) concentration.

Alternatively, a temperature of about 50° C. or more and a high salt (e.g. 'SSPE'=0.180 mM sodium chloride; 9 mM disodium hydrogen phosphate; 9 mM sodium dihydrogen phosphate; 1 mM sodium EDTA; pH 7.4). Preferably the screening is carried out at about 37° C., a formamide concentration of about 20%, and a salt concentration of about 5×SSC, or a temperature of about 50° C. and a salt concentration of about 2×SSPE. These conditions will allow the identification of sequences which have a substantial degree of homology (similarity, identity) with the probe sequence, without requiring the perfect homology for the identification of a stable hybrid.

Suitable conditions include, e.g. for detection of sequences that are about 80–90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90%, identical, suitable conditions include hybridization overnight at 65° C. in 0.25M $Na_2HPO_4$, pH 7.2, 6.50% SDS, 10% dextran sulfate and a final wash at 60° C. in 0.1×SSC, 0.1% SDS.

PCR techniques for the amplification of nucleic acid are described in U.S. Pat. No. 4,683,195 and Saiki et al. Science 239: 487–491 (1988). PCR includes steps of denaturation of template nucleic acid (if double-stranded), annealing of primer to target, and polymerisation. The nucleic acid probed or used as template in the amplification reaction may be genomic DNA, cDNA or RNA. PCR may be used to amplify specific sequences from genomic DNA, specific RNA sequences and cDNA transcribed from mRNA. References for the general use of PCR techniques include Mullis et al, Cold Spring Harbor Symp. Quant. Biol., 51:263, (1987), Ehrlich (ed), PCR technology, Stockton Press, NY, 1989, Ehrlich et al, Science, 252:1643–1650, (1991), "PCR protocols; A Guide to Methods and Applications", Eds. Innis et al, Academic Press, New York, (1990).

Assessment of whether or not a PCR product corresponds to a gene able to alter a plant's characteristics, particularly a flowering characteristic, may be conducted in various ways, as discussed, and a PCR band may contain a complex mix of products. Individual products may be cloned and each screened for linkage to such known genes that are segregating in progeny that showed a polymorphism for this probe. Alternatively, the PCR product may be treated in a way that enables one to display the polymorphism on a denaturing polyacrylamide DNA sequencing gel with specific bands that are linked to the gene being preselected prior to cloning. Once a candidate PCR band has been cloned and shown to be linked to a known flowering gene, it may be used to isolate clones which may be inspected for other features and homologies to ESD4/ESD4 or other related gene. It may subsequently be analysed by transformation to assess its function on introduction into a plant of interest. Alternatively, the PCR band or sequences derived by analysing it may be used to assist plant breeders in monitoring the segregation of a useful gene.

Preferred amino acid sequences suitable for use in the design of probes or PCR primers are sequences conserved (completely, substantially or partly) between at least two ESD4 peptides or polypeptides encoded by genes involved in control of flowering in a plant. Conserved nucleotide sequences may be identified from the nucleotide sequence information contained herein.

On the basis of amino acid sequence information or nucleotide sequence information, oligonucleotide probes or primers may be designed (when working from amino acid sequence information, taking into account the degeneracy of the genetic code and where appropriate, codon usage of the organism).

A gene or fragment thereof identified as being that to which a said nucleic acid molecule hybridises, which may be an amplified PCR may be isolated and/or purified and may be subsequently investigated for ability to alter a flowering characteristic of a plant. If the identified nucleic acid is a fragment of a gene, the fragment may be used (e.g. by probing and/or PCR) in subsequent cloning of the full-length gene, which may be a full-length coding sequence. Inserts may be prepared from partial cDNA clones and used to screen cDNA libraries. The full-length clones isolated may be subcloned into expression vectors and activity assayed by introduction into suitable host cells and/or sequenced. It may be necessary for one or more gene fragments to be ligated to generate a full-length coding sequence.

Molecules found to manipulate genes with ability to alter a plant's flowering characteristics may be used as such, i.e. to alter a flowering characteristic of a plant. Nucleic acid obtained and obtainable using a method as disclosed herein is provided in various aspects of the present inventions.

The present application also provides oligonucleotides based on either an ESD4 nucleotide sequence as provided herein or an ESD4, nucleotide sequence obtainable in accordance with the disclosures and suggestions hereon. The oligonucleotides may be of a length suitable for use as primers in an amplification reaction, or they may be suitable for use as hybridization fishing probes. Preferably an oligonucleotide in accordance with the invention, e.g. for use in nucleic acid amplification, has about 10 or fewer codons (e.g. 6, 7 or 8), i.e. is about 30 or fewer nucleotides in length (e.g. 18, 21 or 24).

The present invention also extends to nucleic acid encoding an ESD4 homologue obtained using a nucleotide sequence derived from that shown in FIG. 1.

The ESD4 gene has a novel sequence. No Arabidopsis genes showing significant homology to ESD4 were identified in public database. However, a region of the ESD4 protein showed homology to Expressed Sequence Tags (ESTs) of unknown function isolated from rice and mammals (FIG. 3) (SEQ ID NO:27).

In certain embodiments, nucleic acid according to the present invention encodes a polypeptide which has homology with all or part of the amino acid sequence shown in FIG. 1, in the terms discussed already above (e.g. for length) which homology is greater over the length of the relevant part (i.e. fragment) than the homology shared between a respective part of the amino acid sequence of FIG. 1 and the EST sequences shown in FIG. 3, and may be greater than about 5% greater, more preferably greater than about 10% greater, more preferably greater than about 20% greater, and more preferably greater than about 30% greater. Thus, to exemplify with reference to one embodiment, nucleic acid encoding an amino acid mutant, variant or derivative of the amino acid sequence shown in FIG. 1 may be provided wherein the encoded amino acid sequence includes a contiguous sequence of about 100 amino acids which has greater homology with a contiguous sequence of 100 amino acids within the amino acid sequence of FIG. 1 than any contiguous sequence of 100 amino acids within an EST sequence such as shown in FIG. 5, preferably greater than about 5% greater homology, and so on.

Similarly, nucleic acid according to certain embodiments of the present invention may have homology with all or part of the nucleotide sequence shown in FIG. 1 or FIG. 2, in the terms discussed already above (e.g. for length), which homology is greater over the length of the relevant part (i.e. fragment) than the homology shared between a respective part of the nucleotide sequence of FIG. 1 or FIG. 2 and FIG. 4A or FIG. 4B and may be greater than about 5% greater, more preferably greater than about 10% greater, more preferably greater than about 20% greater, and more preferably greater than about 30% greater. Thus, to exemplify with reference to one embodiment, nucleic acid may be provided in accordance with the present invention wherein the nucleotide sequence includes a contiguous sequence of about 300 nucleotides (or 100 codons) which has greater homology with a contiguous sequence of 300 nucleotides within the nucleotide sequence of FIG. 1 or FIG. 2 than any contiguous sequence of 100 nucleotides within an EST sequence such as shown in FIG. 4A or FIG. 4B, preferably greater than about 5% greater homology, and so on.

The provision of sequence information for the ESD4 gene of *Arabidopsis thaliana* enables the obtention of homologous sequences from other plant species. In particular, it should be possible to easily isolate ESD4 homologues from related, commercially important Brassica species (e.g. *Brassica nigra, Brassica napus* and *Brassica oleraceae*), as has been done for other flowering time genes isolated from Arabidopsis (e.g CO; WO 96/14414).

Thus, included within the scope of the present invention are nucleic acid molecules which encode amino acid sequences which are homologues of ESD4 of *Arabidopsis thaliana*. Homology may be at the nucleotide sequence and/or amino acid sequence level, as has already been discussed above. A homologue from a species other than *Arabidopsis thaliana* encodes a product which causes a phenotype similar to that caused by the *Arabidopsis thaliana* ESD4 gene, generally including the ability to influence a flowering characteristic such as the timing of flowering. In addition, mutants, derivatives or alleles of these genes may promote or delay flowering compared with wild-type. ESD4 gene homologues may also be identified from economically important monocotyledonous crop plants such as rice and maize. Although genes encoding the same protein in monocotyledonous and dicotyledonous plants show relatively little homology at the nucleotide level, amino acid sequences are conserved. Therefore it is possible to use public sequence databases to identify Arabidopsis, rice or maize cDNA clone sequences that were obtained in random sequencing programmes and share homology to the gene of interest, as has been done for other flowering time genes isolated from Arabidopsis (e.g CO; WO 96/14414). A gene related to ESD4 has been isolated from rice as an expressed sequence tag (FIG. 3). Of course, mutants, derivatives and alleles of these sequences are included within the scope of the present invention in the same terms as discussed above for the *Arabidopsis thaliana* ESD4 gene.

Nucleic acid according to the invention may include a nucleotide sequence encoding a product whose wild-type function is to repress flowering. Reducing the level of expression, as in the esd4 mutant, may be used to accelerate flowering, while increasing the level of expression may be used to delay flowering. The ESD4 gene product is an active repressor of flowering, while genes such as CO and LD encode proteins that promote flowering. The over-expression of the LHY gene delays flowering.

The principal physical characteristic, actually a flowering characteristic, which may be altered using the present invention is the timing of flowering. Reduction in expression of the gene product of the ESD4 gene may be used to promote early flowering (in accordance with the esd4 mutant phenotype), and over-expression may be used to delay flowering. This degree of control is useful to ensure synchronous flowering of male and female parent lines in hybrid production, for example. Another use is to advance or retard the flowering in accordance with the dictates of the climate so as to extend or reduce the growing season. This may involve use of anti-sense or sense regulation, discussed further below.

As noted below, other physical characteristics of plants may be affected by means of expression from nucleic acid according to the present invention.

Nucleic acid according to the invention, such as an ESD4 gene or homologue, may be placed under the control of an externally inducible gene promoter to place the timing of flowering under the control of the user. An advantage of introduction of a heterologous gene into a plant cell, particularly when the cell is comprised in a plant, is the ability to place expression of the gene under the control of a promoter of choice, in order to be able to influence gene expression, and therefore flowering, according to preference. Furthermore, mutants and derivatives of the wild-type gene, eg with higher or lower activity than wild-type, may be used in place of the endogenous gene.

In the present invention, over-expression may be achieved by introduction of the nucleotide sequence in a sense orientation. Thus, the present invention provides a method of influencing a physical e.g. flowering characteristic of a plant, the method including causing or allowing expression of the product (polypeptide or nucleic acid transcript) encoded by heterologous nucleic acid according to the invention from that nucleic acid within cells of the plant.

Down-regulation of expression of a target gene may be achieved using anti-sense technology or "sense regulation" ("co-suppression").

In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) Nature 334, 724–726; Zhang et al,(1992) The Plant Cell 4, 1575–1588, English et al., (1996) The Plant Cell 8, 179–188. Antisense technology is also reviewed in Bourque, (1995), Plant Science 105, 125–149, and Flavell, (1994) PNAS USA 91, 3490–3496.

An alternative is to use a copy of all or part of the target gene inserted in sense, that is the same, orientation as the target gene, to achieve reduction in expression of the target gene by co-suppression. See, for example, van der Krol et al., (1990) The Plant Cell 2, 291–299; Napoli et al., (1990) The Plant Cell 2, 279–289; Zhang et al., (1992) The Plant Cell 4, 1575–1588, and US-A-5,231,020. Further refinements of gene silencing or co-suppression technology may be found in WO95/34668 (Biosource); Angell & Baulcombe (1997) The EMBO Journal 16,12:3675–3684; and Voinnet & Baulcombe (1997) Nature 389: pg 553.

The complete sequence corresponding to the coding sequence (in reverse orientation for anti-sense) need not be used. For example fragments of sufficient length may be used. It is a routine matter for the person skilled in the art to screen fragments of various sizes and from various parts of the coding sequence to optimise the level of anti-sense inhibition. It may be advantageous to include the initiating methionine ATG codon, and perhaps one or more nucleotides upstream of the initiating codon. A further possibility is to target a conserved sequence of a gene, e.g. a sequence that is characteristic of one or more genes, such as a regulatory sequence.

The sequence employed may be about 500 nucleotides or less, possibly about 400 nucleotides, about 300 nucleotides, about 200 nucleotides, or about 100 nucleotides. It may be possible to use oligonucleotides of much shorter lengths, 14–23 nucleotides, although longer fragments, and generally even longer than about 500 nucleotides are preferable where possible, such as longer than about 600 nucleotides, than about 700 nucleotides, than about 800 nucleotides, than about 1000 nucleotides or more.

It may be preferable that there is complete sequence identity in the sequence used for down-regulation of expression of a target sequence, and the target sequence, though total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a mutant, derivative, variant or allele, by way of insertion, addition, deletion or substitution of one or more nucleotides, of such a sequence. The sequence need not include an open reading frame or specify an RNA that would be translatable. It may be preferred for there to be sufficient homology for the respective anti-sense and sense RNA molecules to hybridise. There may be down regulation of gene expression even where there is about 5%, 10%, 15% or 20% or more mismatch between the sequence used and the target gene.

Generally, the transcribed nucleic acid may represent a fragment of an ESD4 gene, such as including a nucleotide sequence shown in FIG. 1 or FIG. 2, or the complement thereof, or may be a mutant, derivative, variant or allele thereof, in similar terms as discussed above in relation to alterations being made to an ESD4 coding sequence and the homology of the altered sequence. The homology may be sufficient for the transcribed anti-sense RNA to hybridise with nucleic acid within cells of the plant, though irrespective of whether hybridisation takes place the desired effect is down-regulation of gene expression.

Thus, the present invention also provides a method of influencing a flowering characteristic of a plant, the method including causing or allowing anti-sense transcription from heterologous nucleic acid according to the invention within cells of the plant.

The present invention further provides the use of the nucleotide sequence of FIG. 1 or FIG. 2 or a fragment, mutant, derivative, allele, variant or homologue thereof for down-regulation of gene expression, particularly down-regulation of expression of an ESD4 gene or homologue thereof, preferably in order to influence a physical characteristic of a plant, especially a flowering characteristic such as the timing of flowering.

When additional copies of the target gene are inserted in sense, that is the same, orientation as the target gene, a range of phenotypes is produced which includes individuals where over-expression occurs and some where under-expression of protein from the target gene occurs. When the inserted gene is only part of the endogenous gene the number of under-expressing individuals in the transgenic population increases. The mechanism by which sense regulation occurs, particularly down-regulation, is not well-understood. However, this technique is also well-reported in scientific and patent literature and is used routinely for gene control. See, for example, van der Krol et al., (1990) The Plant Cell 2, 291–229; Napoli et al., (1990) The Plant Cell 2, 279–289; Zhang et al, 1992 The Plant Cell 4, 1575–1588.

Again, fragments, mutants and so on may be used in similar terms as described above for use in anti-sense regulation.

Thus, the present invention also provides a method of influencing a flowering characteristic of a plant, the method including causing or allowing expression from nucleic acid according to the invention within cells of the plant. This may be used to suppress activity of a product with ability to influence a flowering characteristic. Here the activity of the product is preferably suppressed as a result of under-expression within the plant cells.

Reduction of gene activity may also be achieved by using ribozymes, such as replication ribozymes, e.g. of the hammerhead class (Haseloff and Gerlach, 1988, Nature 334: 585–591; Feyter et al. Mol., 1996, Gen. Genet. 250: 329–338).

Another way to reduce gene activity in a plant employs transposon mutagenesis (reviewed by Osborne et al., (1995) Current Opinion in Cell Biology 7, 406–413). Inactivation of genes has been demonstrated via a "targeted tagging" approach using either endogenous mobile elements or heterologous cloned transposons which retain their mobility in alien genomes. Alleles carrying any insertion of known sequence may be identified by using PCR primers with binding specificities both in the insertion sequence and the homologue. "Two-element systems" may be used to stabilize the transposon within inactivated alleles. In the two-element approach, a T-DNA is constructed bearing a non-autonomous transposon containing selectable or screenable marker gene inserted into an excision marker. Plants bearing these T-DNAs are crossed to plants bearing a second T-DNA expressing transposase function. Hybrids are double-selected for excision and for the marker within the transposon yielding $F_2$ plants with transposed elements.

Early flowering caused by reduced expression of the ESD4 gene

As described in Example 1, the esd4 mutation causes early flowering under long and short day conditions and is caused by a deletion that decreases expression of the gene. Example demonstrates that introduction of the ESD4 gene into the mutant is sufficient to correct the defect caused by the mutation. This provides indication that the function of the ESD4 gene is to repress flowering and that reduction in its function causes the plant to flower early.

Causing late flowering by increasing the activity of ESD4 The observation that reduced expression of the ESD4 gene accelerates flowering provides indication that the normal function of ESD4 is to delay flowering. Increasing the expression of the ESD4 gene is indicated for use in causing late flowering. This is supported by the observation that in wild-type plants the ESD4 mRNA is rare; it was only detected by RT-PCR and is absent from libraries of randomly sequenced cDNAs. Increasing the level of the ESD4 mRNA by expressing the gene from strong plant promoters such as the CaMV 35S promoter may be used to cause late flowering.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE DRAWINGS

FIG. 1 shows a nucleotide sequence (SEQ ID NO:14) according to one embodiment of the invention, being the sequence of the ESD4 ORF, obtained from *Arabidopsis thaliana*, with the predicted amino acid sequence (SEQ ID NO:15) shown below the said nucleotide sequence. This is the cDNA sequence obtained from the Columbia ecotype.

FIGS. 2A–2C show the genomic sequence of the ESD4 gene. This includes the coding sequence, the introns, the likely promoter region extending upstream of the start of translation and sequence extending approximately 4.0 kb after the translation stop. The translational start and stop codons are double underlined. The sequence shown in italics and in lower case is deleted in the esd4 mutant. The sequence underlined was absent in the original ESSA sequence. The underlined sequence is from Landsberg erecta ecotype and was used to repair the ESSA sequence, while the remainder of the sequences is from Columbia ecotype. (SEQ ID NO:16.)

FIG. 3 shows a comparison of the ESD4 protein sequence of FIG. 1 with predicted translation products from rice and mammalian ESTS. Identical residues are shown in black boxes, related ones in hatched boxes. The ESD4 protein sequence shown starts at residue 231 and extends to the end of the protein. (SEQ ID NO:17-SEQ ID NO:22, SEQ ID NO:27, SE ID NO:23 and SEQ ID NO:24.)

FIG. 4A shows the nucleotide sequence of the rice EST for which the predicted encoded amino acid sequence is shown in FIG. 3. (SEQ ID NO:25.)

FIG. 4B shows the nucleotide sequence of the human EST for which the predicted encoded amino acid sequence is shown in FIG. 3. (SEQ ID NO:26.)

EXAMPLE 1

Cloning and Analysis of an esd4 Gene

Identification of the esd4 mutant in a population of gamma-ray mutagenised plants.

Dry seeds of *Arabidopsis thaliana* were exposed to 90 krads of gamma rays. These were germinated on soil, germinated and the M1 plants grown to maturity. These plants were self-fertilised and the M2 seeds harvested. These were germinated on soil and the plants grown under short days of 10 hours light. Wild-type plants flower late under these conditions, and therefore early flowering mutants can be easily recognised. The esd4. mutant was the earliest flowering plant recovered in this population. The mutant was self-fertilised, and its progeny grown to confirm the mutant phenotype. The mutant was then back-crossed twice to wild-type to reduce the possibility that mutations other than esd4 were also present.

Description of the esd4 Mutant Phenotype

The esd4 mutant flowers significantly earlier than wild-type under long and short days, although the difference is most dramatic under short days (Table 1). The esd4 mutant retains sensitivity to daylength, flowering earlier under long than short days.

In addition to its effect on flowering time, the esd4 mutant shows some pleiocropic effects. The mutants are shorter than wild-type and produce fewer flowers. In addition, the mutant forms flowers or floral structures in ectopic positions on the shoot. These ectopic floral structures occur in two ways. First, the shoot meristem is converted late in development into a carpelloid structure, so that the shoot is determinate and terminates with this structure. Second, extra flowers are formed on the sides of the shoot. Either one or several flowers are often formed very close to the position of the last cauline leaf, where flowers are never in wild-type plants, or at the first node at which flowers are formed several flowers develop rather than only one. These phenotypes indicate that ESD4 has a role in ensuring that flowers form in their correct positions.

The esd4 mutation also has an effect on pod shape. The siliques of mutant plants are noticeably club shaped, being narrow at the base and broad at the tip, while in wild-type plants they are of similar width throughout their length.

Location of ESD4 in the *Arabidopsis genome*

The location of the ESD4 gene was determined by testing for genetic linkage between the mutation and DNA markers that are polymorphic between the Arabidopsis ecotypes Landsberg erecta and Columbia. The esd4 mutant was crossed to the Columbia ecotype, and F1 plants grown to maturity. The F1 plants were self-fertilised and F2 progeny grown in the greenhouse under short days. F2 plants that showed the homozygous esd4 phenotype were identified, and DNA was extracted from 30 of these individuals. Published RFLP and CAPS markers of known position were tested for genetic linkage to esd4. Loose linkage was detected with markers m448 and nga8 which are located on chromosome 4, and tighter linkage was found with AG, which is positioned lower on chromosome 4. The number of esd4 mutant plants tested was then increased to 250, and more markers located between nga8 and AG were tested. This demonstrated that esd4 is located on chromosome 4 between markers m326 and SC5, an interval of approximately 3 cM.

Fine Mapping of ESD4

With the aim of identifying the ESD4 gene it was decided to increase the resolution of the mapping and identify cosmid clones containing ESD4. Cosmid DNA was introduced into the esd4 mutant to try to demonstrate the exact location of the ESD4 gene. A total of 891 plants that were homozygous for esd4 were recovered in the F2 of a cross between Columbia and the original esd4 mutant. DNA was extracted from these plants, and they were all scored with the SC5 and m326 markers shown to flank the gene. A total of approximately 43 recombinant chromosomes were found with recombination points mapping between m326 and ESD4, and 10 were found with recombination points mapping between SC5 and ESD4. Recombinant plants were then tested with markers located between SC5 and m326. Markers were identified in this region by scanning the physical map of the region. An unpublished cosmid contig that included SC5 and extended to approximately 250 kb from m326 was employed. We selected from this contig cosmids at defined positions and used these as RFLP markers. Ultimately this contig as well as unpublished sequence information obtained in confidence from the cosmids by the EC funded programme European Sequencers Sequencing Arabidopsis (ESSA), a purely sequencing programme, enabled us to locate esd4 between polymorphisms detected with cosmids G5945 and G14587. These two cosmids overlap i.e. they contain some DNA in common. The region between the polymorphisms was only approximately 35 kb in length and was defined by one plant that carried a recombination cross-over between esd4 and a CAPS marker G14 (primers G14F (SEQ ID NO:1) and G14R) (SEQ ID NO:2) at one end of G14587 and 3 plants that carried cross-overs between esd4 and CAPS marker G32 (primers G32F (SEQ ID NO:3) and G32R) (SEQ ID NO:4) which is at the other end of G14587.

With the aim of identifying the ESD4 gene it was decided to increase the resolution of the mapping and identify cosmid clones containing ESD4. Cosmid DNA was introduced into the esd4 mutant to try to demonstrate the exact location of the ESD4 gene. A total of 891 plants that were homozygous for esd4 were recovered in the F2 of a cross between Columbia and the original esd4 mutant. DNA was extracted from these plants, and they were all scored with the SC5 and m326 markers shown to flank the gene. A total of approximately 43 recombinant chromosomes were found with recombination points mapping between m326 and ESD4, and 10 were found with recombination points mapping between SC5 and ESD4. Recombinant plants were then tested with markers located between SC5 and m326. Markers were identified in this region by scanning the physical map of he region. An unpublished cosmid contig that included SC5 and extended to approximately 250 kb from m326 was employed. We selected from this contig cosmids at defined positions and used these as RFLP markers. Ultimately this contig as well as unpublished sequence information obtained in confidence from the cosmids by the EC funded programme European Sequencers Sequencing Arabidopsis (ESSA), a purely sequencing programme, enabled us to locate esd4 between polymorphisms detected with cosmids G5945 and G14587. These two cosmids overlap i.e. they contain some DNA in common. The region between the polymorphisms was only approximately 35 kb in length and was defined by one plant that carried a recombination cross-over between esd4 and a CAPS marker G14 (primers G14F (SEQ ID NO:1) and G14R) (SEQ ID NO:2) at one end of G14587 and 3 plants that carried cross-overs between esd4 and CAPS marker G32 (primers G32F (SEQ ID NO:3) and G32R) (SEQ ID NO:4) which is at the other end of G14587.

Identification of the ESD4 Gene by Complementation and Sequencing of the Mutant Allele The genetic experiments described in the previous section located ESD4 to a region approximately 35 kb long. With the aim of locating the gene more accurately it was decided to introduce overlapping fragments of DNA from within this region into esd4 mutant plants to determine which were capable of correcting the esd4 mutant phenotype.

The complementation experiments could not be performed with the G5945 and G14587 cosmids because these were not made in a cosmid vector that could be used for plant transformation. The cosmid vector 04541 which is also a binary vector that could be used for plant transformation was used. With the aim of identifying 04541-based cosmids containing the relevant DNA an 04541-based cosmid library made from YAC YUPSB11 was used. This YAC spans the whole region demonstrated to contain the ESD4 gene. The cosmid library was screened with probes made from cosmids G5945 and G14587. Positively hybridising clones were then mapped with restriction enzymes HindIII and SalI and from these digestions the positions of the clones relative to one another could be determined.

A series of four overlapping clones (G8, P9, P7 and P14) were then used for complementation studies by introducing them into esd4 mutant plants. The G8 and P7 clones complemented the mutation (Table 2, Table 3, Table 4), indicating that the gene is located in the approximately 10 kb of DNA shared by these cosmids. The complementation was almost complete, but not entirely, especially under short days. This might be because of position effects of the transgene or because the transgene is from Columbia and the mutation in Landsberg erecta or because there is another mutation in the esd4 background in addition to esd4 which also causes early flowering. The sequence of the region shared by the two cosmids was obtained by us in confidence from the EC-funded programme European Sequencers Sequencing Arabidopsis (ESSA), but has not been made available to the public.

Comparison of the sequence from ESSA with the HindIII restriction map of the cosmid revealed an anomaly. We found that a HindIII restriction fragment in the cosmid was 4.4 kb long, but from the sequence was predicted to be only 4.0 kb. To test this further we amplified by PCR the anomalous region (using primers SMR (SEQ ID NO:5) and SMF) (SEQ ID NO:6) and sequenced the amplified fragment from Landsberg erecta DNA (FIG. 2).

This demonstrated that the ESSA sequence was not correct in this critical region and that 424 bp of DNA was deleted from the sequence. The corrected sequence is shown in FIG. 2.

Computer analysis did not detect homology to any previously published plant gene in the region of overlap of the two complementing cosmids. However, use of the GENEFINDER and GRAIL programmes did predict that this region was likely to encode one gene based on the presence of open reading frames within the genomic sequence and of likely exon/intron splice junctions. It seemed likely that this was the ESD4 gene.

Further evidence for this was obtained by analysing DNA isolated from the esd4 mutant. Use of the polymerase chain reaction and primers A (GTCTCATAGGCGTCTTTG) (SEQ ID NO:7) and P2 (CATACCAGAGCATTCAGAATC) (SEQ ID NO:8) demonstrated that the esd4 mutant had suffered a 762 bp deletion in the region of the predicted ESD4 gene. The computer analysis of the ESD4 region predicted that this deletion had removed 10 codons from the protein coding sequence and part of the promoter region. The deleted DNA is marked in FIG. 2. The presence of this deletion in the esd4 mutant strongly suggested that this region encodes the ESD4 gene.

Gene Structure

To confirm the structure of the ESD4 gene that was predicted from the computer analysis, a cDNA was screened for in cDNA Elibraries. The aerial parts library and a seedling library were screened by PCR using primers that annealed to the vector. Small fragments were amplified from these libraries andsequenced. The libraries were then re-screened using primers that annealed to the ESD4 sequence and were designed from either the genomic sequence or the cDNA sequence that had already been obtained. The fragments were sequenced by cycle sequencing.

This combination of approaches produced an entire cDNA sequence which is shown in FIG. 1, and is the sequence of the ESD4 open reading frame produced from Columbia.

Primers that annealed to close to the predicted translational stop sequence (C3 new) (SEQ ID NO:9) and to the predicted translational start sequence (C5) (SEQ ID NO:10) were synthesised to use for RT-PCR and thereby to confirm that the transcript is present in wild-type plants. These were then used in a PCR to amplify DNA from first strand cDNA. The cDNA had previously been synthesised from RNA extracted from Arabidopsis seedlings at the 2 leaf stage. An amplified fragment of the predicted size (approximately 1.5 kb) was obtained and hybridised to the ESD4 cDNA.

Attempts to clone the entire cDNA into the *E.coli* Bluescript plasmid initially failed. However, it was subcloned in two pieces. The primers (1SO (SEQ ID NO:11) and 2SO) (SEQ ID NO:12) were used to amplify the 5' end of the gene and it was cloned into the XbaI and SpeI sites of Bluescript. The 3' end was cloned using primers (3SO (SEQ ID NO:13) and c3new) and this was then cloned into the SpeI and BamHI sites of Bluescript. The two fragments were then joined together by ligating the fragments at the common SpeI site by inserting the 3' fragment into the SpeI and BamHI sites of the 5' clone.

Figure 3:
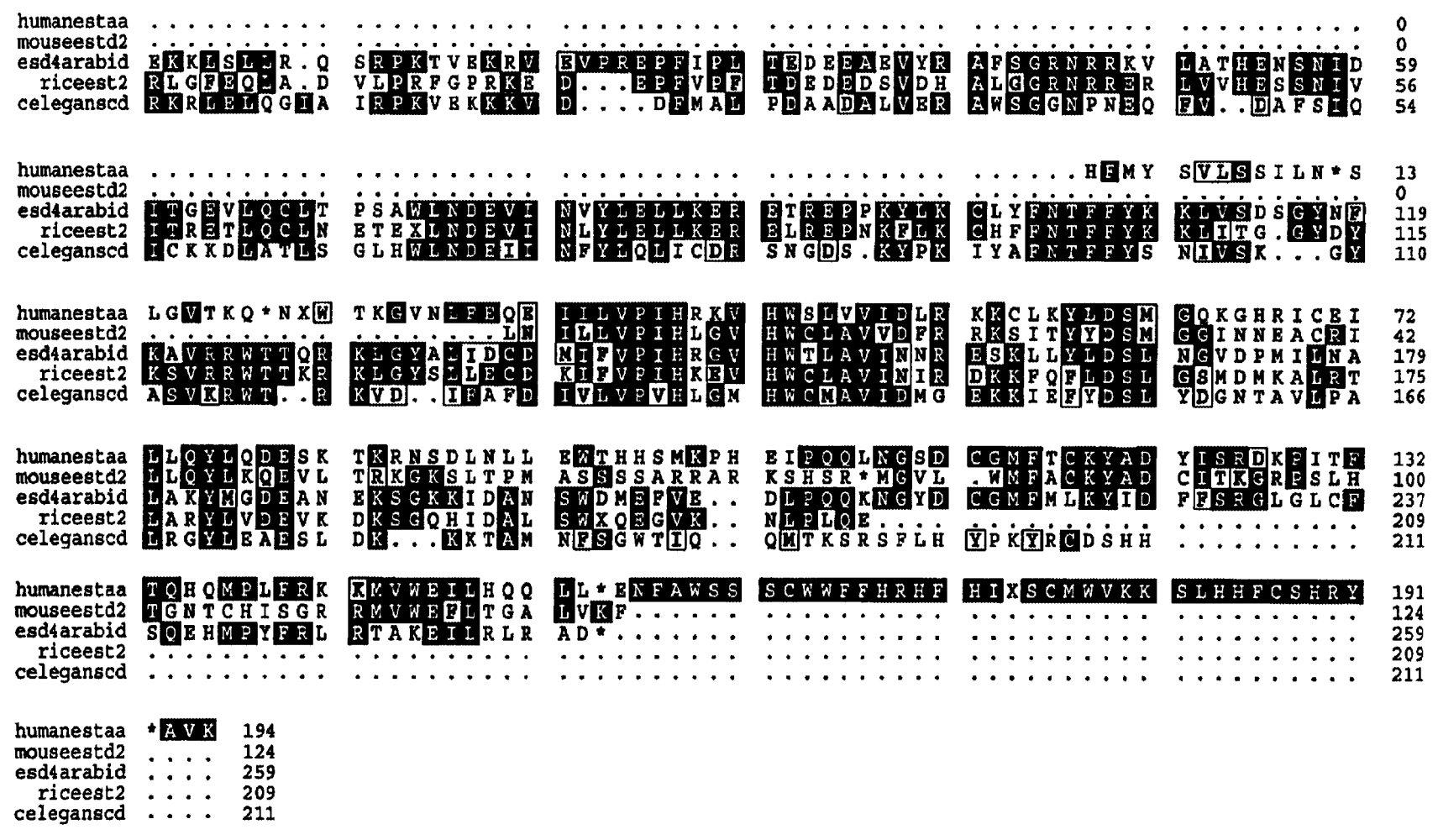

Comparison of ESD4 to other sequences in the databases. The ESD4 cDNA and predicted protein sequence were used to search for homology to genes in the public databases. Using a BLAST search of GenBank homology to the carboxy-terminal region of ESD4 was found to genes from rices, *C.elegans*, humans and rouse (FIG. 3) (SEQ ID NO:27). The residues shared by these proteins can be presumed to define a functional domnain of the protein.

METHODS

Growth conditions and measurement of flowering time Flowering time was measured under defined conditions by growing plants in Sanyo Gallenkamp Controlled Environment rooms at 20° C.

Short days comprised a photoperiod of 10 hours lit with 400 Watt metal halide power star lamps supplemented with 100 watt tungsten halide lamps. This provided a level of photosynthetically active radiation (PAR) of 113.7 _moles photons $m^{-2}s^{-1}$ and a red:far red light ration of 2.41. A similar cabinet and lamps were used for the long day. The photoperiod was for 10 hours under the same conditions used for short days and extended for a further 8 hours using only the tungsten halide lamps. In this cabinet the combination of lamps used for the 10 hour period provided a PAR of:92.9 _moles photons $m^{-2}$ $s^{-1}$ and a red:far red ratio of 1.49. The 8 hour extension produced PAR of 14.27 _moles $m^{-2}$ $s^{-1}$ and a red:far-red ratio of 0.66.

The flowering times of large populations of plants were measured in the greenhouse. In the summer the plants were simply grown in sunlight. In winter supplementary light was provided so that the minimum daylength was 16 hours.

To measure flowering time, seeds were placed at 4° C. on wet filter paper for 4 days to break dormancy and were then sown on soil. Germinating seedlings were usually covered with clingfilm or propagator lids for the first 1–2 weeks to prevent dehydration. Flowering time was measured by counting the number of leaves, excluding the cotyledons, in the rosette at the time the flower bud was visible. Leaf numbers are shown with the standard error at 95% confidence limits. The number of days from sowing to the appearance of the flower bud was also recorded, but is not shown.

Plant Material

The standard wild-type genotype used was *Arabidopsis thaliana* Landsberg, erecta.

Isolation of Plant Genomic DNA

Plant genomic DNA was isolated from glasshouse grown plants essentially as described by Tai and Tanksley, *Plant Mol. Biol. Rep.* 8: 297–303. (1991), except that the tissue was ground in liquid nitrogen and the RNase step omitted. Large-scale (2.5–5 g leaves) and miniprep (3–4 leaves) DNA was prepared using this method.

Gel Blotting and Hybridisation Conditions

Gel transfer to Hybond-N, hybridisation and washing conditions were according to the manufacturer's instructions, except that DNA was fixed to the filters by UV Stratalinker treatment (1200 uJ×100; Stratagene) and/or baked at 80° C. for 2 h. Radiolabelled DNA was prepared by random hexamer labelling.

RFLP and CAPS Markers

All information relating to RFLP markers and CAPS markers that are described in the text but were received from other labs are described in Arabidopsis thaliana Database or Arabidopsis Management Information Service on the internet (Stanford genome website at Arabidopsis, or at aims (dot) cps (dot) msu (doe) edu (forward slash) aims (forward slash) menu (forward slash) catalog).

The crucial CAPS markers G14 and G32 which most closely flank ESD4 and were used to position the gene most accurately are described in the text and the sequences of the primers used are provided. In each case a polymorphism was detected between Landsberg erecta and Columbia: with the G14 fragment with ClaI and with the G32 fragment with EcoRV.

RNA Extractions

RNA was extracted using a method which is a modified version of that described by Stiekema et al., (1988) Plant Molecular Biology 11, 255–269. Approximately 5 g of tissue frozen in liquid nitrogen was ground in a coffee grinder and extracted with a mixture of 15 ml of phenol and 15 ml of extraction buffer (50 mM Tris pH8, 1 mM EDTA, 1% SDS). The mixture was shaken, centrifuged and 25 ml of the aqueous layer recovered. This was then shaken vigorously with a mixture of 0.7 ml 4M sodium chloride, 10 ml phenol and 10 ml of chloroform. The aqueous layer was recovered after centrifugation and extracted with 25 ml of chloroform. The RNA was then precipitated from 25 ml of the aqueous layer by the addition of 2 ml of 10 M LiCL, and the precipitate recovered by centrifugation. The pellet was dissolved in 2 ml DEPC water and the RNA precipitated by the addition of 0.2 ml of 4M sodium chloride and 4 ml of ethanol. After centrifugation the pellet was dissolved in 0.5 ml of DEPC water and the RNA concentration determined.

DNA Extractions

Arabidopsis DNA was performed by a CTAB extraction method described by Dean, et al. (1992), *Plant Journal*, 2: 69–82.

Isolation of cDNA by RT-PCR

Total RNA was isolated from whole seedlings at the 2–3 leaf stage growing under long days in the greenhouse. For first strand cDNA synthesis, 10 ug of RNA in a volume of 10 ul was heated to 65° C. for 3 minutes, and then quickly cooled on ice. 10 ul of reaction mix was made containing 1 ul of. RNAsin, 1 ul of standard $dT_{17}$-adapter primer (1 ug/ul; Frohman et al, 1988), 4 ul of 5× reverse transcriptase buffer (250 mM TrisHCl pH8.3, 375 mM KCl, 15 mM $MgCl_2$), 2 ul DTT (100 mM) 1 ul dNTP (20 mM), 1 ul reverse transcriptase (200 units, M-MLV Gibco). This reaction mix was then added to the RNA creating a final volume of 20 ul. The mixture was incubated at 42° C. for 2 hours and then diluted to 200 ul with water. The first strand cDNA was then used for PCR using primers C3new and C5, 1SO and 2SO or 3SO and 4So that are described above and the reactions were performed at 94° C. for 1 minute, 34 cycles of 55° C. for 1 minute, 72° C. for 2 minutes and then finally at 72° C. for 10 minutes.

20 ul of the reaction was separated through an agarose gel, and the presence of a fragment of the expected size was demonstrated after staining with ethidium bromide. The DNA was transferred to a filter, and the fragment of interest was shown to hybridise to a short DNA fragment derived from the ESD4 gene.

Transformation of Arabidopsis

The cosmids containing DNA from the vicinity of LHY were mobilised into; Agrobacterium tumefaciens C58C1, and the T-DNA introduced into *Arabidopsis plants* as described by Valvekens, et al, (1988), *Proc. Natl. Acad. Sci, USA*, 87: 5536–5540. Roots of plants grown in vitro were isolated and grown on callus-inducing medium (Valvekens et al, 1988) for 2 days. The roots were then cut into short segments and co-cultivated with *Agrobacterium tumefaciens* carrying the plasmid of interest. The root explants were dried on blotting paper and placed onto callus-inducing medium for 2–3 days. The Agrobacterium were washed off, the roots dried and placed onto shoot inducing medium (Valvekens et al, 1988) containing vancomycin to kill the Agrobacterium and kanamycin to select for transformed plant cells.

After approximately 6 weeks green calli on the roots started to produce shoots. These were removed and placed in petri dishes or magenta pots containing germination medium (Valvekens et al, 1988). These plants produced seeds in the magenta pots. These were then sown on germination medium containing kanamycin to identify transformed seedlings containing the transgene (Valvekens et al, 1988), and to assess the number of loci at which a transgene is inserted.

The resistant plants were then grown to maturity and self-fertilised. Plants homozygous for the T-DNA were identified by sowing the seeds of each plant on kanamycin-containing medium and selecting those in which all of the progeny were kanamycin resistant. The flowering times of plants in these families were then measured by sowing the appropriate seeds directly on soil.

TABLE 1

Flowering times of esd4 mutant and wild-type plants under long and short days. The herterozygotes behave like wild-type indicating that the esd4 mutation is recessive.

| | Long Days | | Short Days | |
|---|---|---|---|---|
| Genotype | Rosette Leaves | Cauline Leaves | Rosette Leaves | Cauline Leaves |
| Landsberg erecta | 5.4 ± 0.5 | 3.1 ± 0.2 | 29.7 ± 2.2 | 6.6 ± 1.2 |
| esd4 | 2.0 ± 0.0 | 2.0 ± 0.0 | 3.2 ± 0.5 | 2.0 ± 0.0 |
| esd4/+ | 5.0 ± 0.4 | 3.1 ± 0.7 | 28.9 ± 2.0 | 7.5 ± 1.7 |

In the experiments for which results are reported in Tables 2 and 3, plants scored were the progeny of the primary transformants. One batch of seeds was sown on kanamycin medium and the seedlings scored for kanamycirn resistance, and the ratio of sensitive to resistant seedlings is shown. A second batch of seeds was sown on soil and scored for flowering time by counting leaf number. Because the transgene was segregating, some plants looked like esd4 as they had not inherited the transgene. The ratio of wild-type plants to the total number of plants in the population is shown in the final column.

TABLE 2

Flowering times of transgenic esd4 mutant plants carrying a transgenic copy of the ESD4 gene (YUP5B11.IB3C12) on cosmid G8 grown under long days.

| Trans-formant | Kanamycin Resistant | Kanamycin Sensitive | Rosette Leaves | Cauline Leaves | N |
|---|---|---|---|---|---|
| esd4 control | 0 | 14 | 2.1 ± 0.4 | 2.7 ± 0.5 | 27/27 |
| Landsberg erecta | 0 | 23 | 6.7 ± 0.8 | 3.3 ± 0.5 | 32/32 |
| G8:1–7 | 30 | 7 | 6.2 ± 0.7 | 2.9 ± 0.5 | 33/36 |
| G8:1–9 | 38 | 16 | 5.9 ± 0.6 | 2.8 ± 0.5 | 29/33 |
| G8:1–10 | 33 | 15 | ND | ND | ND |
| G8:1–12 | 19 | 5 | 5.5 ± 0.7 | 2.7 ± 0.7 | 21/27 |
| GS:1–16 | ND | ND | 4.5 ± 0.7 | 2.0 ± 0.0 | 2/28 |
| G8:1–18 | 3 | 32 | 4.0 ± 0.0 | 2.0 ± 0.0 | 1/39 |
| G8:1–20 | 22 | 5 | 4.7 ± 0.6 | 2.3 ± 0.7 | 26/28 |
| G8:1–21 | 47 | 16 | 6.0 ± 0.5 | 2.7 ± 0.5 | 31/39 |
| G8:1–23 | 41 | 17 | 5.5 ± 0.6 | 2.6 ± 0.5 | 33/38 |
| GB:1–24 | 27 | 10 | ND | ND | ND |
| G8:1–25 | 35 | 10 | 6.3 ± 0.8 | 2.3 ± 0.7 | 26/33 |
| G8:1–34 | 43 | 8 | 5.6 ± 0.8 | 2.5 ± 0.5 | 14/22 |
| G8:2–21 | 33 | 10 | 5.7 ± 0.7 | 2.8 ± 0.6 | 28/34 |
| G8:2–22 | 50 | 11 | 5.6 ± 0.6 | 2.7 ± 0.5 | 31/39 |
| G8:2–23 | 23 | 9 | 5.4 ± 0.5 | 2.5 ± 0.7 | 17/23 |

TABLE 3

Flowering times of transgenic esd4 mutant plants carrying a transgenic copy of the ESD4 gene (YUP5B11.IB1E13) on cosmid P7 grown under long days.

| Trans-formant | Kanamycin Resistant | Kanamycin Sensitive | Rosette leaves | Cauline leaves | N |
|---|---|---|---|---|---|
| esd4 +ve control | — | — | 2.5 ± 0.6 | 2.4 ± 0.6 | 29/29 |
| Landsberg erecta | — | — | 6.3 ± 0.6 | 3.1 ± 0.6 | 28/28 |
| P7:16–1 | 32 | 6 | 4.7 ± 0.5 | 2.3 ± 0.5 | 29/38 |
| P7:16–2 | 88 | 4 | 5.8 ± 0.9 | 3.2 ± 0.5 | 38/39 |
| P7:16–3 | 42 | 6 | 5.2 ± 0.5 | 3.1 ± 0.3 | 38/40 |

TABLE 3-continued

Flowering times of transgenic esd4 mutant plants
carrying a transgenic copy of the ESD4 gene
(YUP5B11.IB1E13) on cosmid P7 grown under long days.

| Trans-formant | Kanamycin Resistant | Kanamycin Sensitive | Rosette leaves | Cauline leaves | N |
|---|---|---|---|---|---|
| P7:16–4 | 65 | 2 | 5.0 ± 0.3 | 2.7 ± 0.5 | 30/40 |
| P7:16–7 | 86 | 10 | 5.5 ± 0.6 | 2.7 ± 0.5 | 38/39 |
| P7:16–8 | 43 | 14 | 5.7 ± 0.9 | 2.0 ± 0.6 | 34/40 |
| P7:16–16 | 58 | 13 | 5.3 ± 0.6 | 2.8 ± 0.5 | 31/37 |
| P7:16–17 | 70 | 15 | 5.2 ± 0.6 | 2.9 ± 0.4 | 35/38 |
| F7:16–18 | 24 | 11 | 5.5 ± 0.6 | 3.2 ± 0.5 | 39/40 |
| P7:18–6 | 60 | 11 | 5.2 ± 0.5 | 3.0 ± 0.4 | 33/38 |
| P7:18–12 | 48 | 12 | 5.0 ± 0.3 | 2.9 ± 0.4 | 34/30 |
| P7:18–13 | 43 | 2 | 5.1 ± 0.5 | 2.9 ± 0.4 | 38/40 |
| P7:18–15 | 55 | 9 | ND | ND | ND |

TABLE 4

Flowering times of transgenic esd4 mutant plants
homozygous for a copy of the ESD4 gene (YUP5B11.IB3C12)
on cosmid G8 and grown under long and short days. Plants
homozygous for the transgene were identified among the
progeny of the initial transformants. The progeny of
these homozygous plants were used for the experiment.

| | Long Days | | Short Days | |
|---|---|---|---|---|
| Transformant | Rosette Leaves | Cauline Leaves | Rosette Leaves | Cauline Leaves |
| Landsberg erecta | 5.4 ± 0.5 | 3.1 ± 0.2 | 29.7 ± 2.2 | 6.6 ± 1.2 |
| esd4 | 2.0 ± 0.0 | 2.0 ± 0.0 | 3.2 ± 0.5 | 2.0 ± 0.0 |
| G8:1–7 | 4.1 ± 0.3 | 2.6 ± 0.5 | 16.9 ± 1.2 | 4.3 ± 1.3 |
| G8:1–9 | 4.6 ± 0.5 | 2.7 ± 0.5 | 19.9 ± 1.9 | 6.9 ± 1.4 |
| G8:1–12 | 4.2 ± 0.4 | 2.4 ± 0.6 | 15.3 ± 1.2 | 4.6 ± 1.0 |
| G8:1–20 | 4.4 ± 0.5 | 2.8 ± 0.4 | 17.4 ± 1.8 | 4.9 ± 0.8 |
| G8:1–21 | 4.2 ± 0.4 | 2.8 ± 0.6 | 17.1 ± 2.2 | 5.6 ± 0.7 |
| G8:1–25 | 4.2 ± 0.4 | 3.1 ± 0.4 | 19.9 ± 1.5 | 6.7 ± 0.7 |
| G8:1–34 | 4.1 ± 0.3 | 2.8 ± 0.4 | 17.0 ± 1.6 | 5.2 ± 0.9 |
| G8:2–23 | 4.0 ± 0.0 | 2.3 ± 0.6 | 14.7 ± 1.9 | 4.9 ± 0.9 |

What is claimed is:

1. An isolated nucleic acid encoding a polypeptide which comprises the amino acid sequence shown in FIG. 1 (SEQ ID NO:15).

2. The nucleic acid according to claim 1 wherein said nucleic acid comprises nucleotides 100 to 1566 of SEQ ID NO:14.

3. The nucleic acid according to claim 1 wherein said nucleic acid comprises a coding sequence which differs from nucleotides 100 to 1566 of SEQ ID NO:14 but encodes the amino acid sequence shown in FIG. 1 (SEQ ID NO:15).

4. An isolated nucleic acid encoding a polypeptide, wherein transgenic expression of said polypeptide in a esd4 mutant Arabidopsis plant complements the early flowering phenotype of said plant, and wherein said isolated nucleic acid is capable of hybridizing with a probe from the sequence of SEQ ID NO: 14 under the following screening conditions: hybridization at 65° C. in 0.25M $Na_2PHO_4$, pH 7.2, 6.5% SDS, 10% dextran sulfate and a final wash at 60° C. in 0.1×SSC, 0.1% SDS.

5. The nucleic acid according to claim 1 operably linked to a regulatory sequence.

6. The nucleic acid according to claim 5 wherein the regulatory sequence comprises an inducible promoter.

7. An isolated nucleic acid which is a fragment of the nucleic acid of claim 2, wherein said isolated nucleic acid is operably linked to a regulatory sequence for transcription in a plant cell, and which is suitable, when expressed in a transgenic plant, to co-suppress an endogenous ESD4 gene and promote the timing of flowering of the transgenic plant.

8. An isolated nucleic acid having a nucleotide sequence complementary to the nucleic acid of claim 2 or a fragment thereof, wherein the complementary nucleotide sequence is operably linked to a regulatory sequence for transcription in a plant cell, and wherein the complementary nucleotide sequence is suitable, when expressed in a transgenic plant, to inhibit the expression of an endogenous ESD4 gene and promote the timing of flowering of the transgenic plant.

9. The nucleic acid according to claim 8 wherein the regulatory sequence comprises an inducible promoter.

10. A nucleic acid vector suitable for transformation of a plant cell and comprising the nucleic acid according to claim 1.

11. A host cell which is a microbial cell, containing as a heterologous nucleic acid the nucleic acid according to claim 1.

12. A host cell which is a plant cell, containing as a heterologous nucleic acid the nucleic acid according to claim 1.

13. The host cell according to claim 12 wherein said heterologous nucleic acid is within the genome of said plant cell.

14. The plant cell according to claim 13 having more than one said nucleic acid per hapoloid genome.

15. A transgenic plant comprising the plant cell according to claim 12.

16. The plant according to claim 15 which does not breed true.

17. A part or propagule of a plant said part or propagule comprising the host cell according to claim 12.

18. A method of promoting flowering time of a plant, the method comprising expressing a nucleic acid heterologous to said plant, wherein said nucleic acid heterologous to said plant is the nucleic acid according to claim 7, wherein expression of said nucleic acid in said plant promotes the timing of flowering.

19. A method of promoting flowering time of a plant, the method comprising expressing a nucleic acid heterologous to said plant, wherein said nucleic acid heterologous to said plant is the nucleic acid according to claim 8, wherein expression of said nucleic acid in said plant promotes the timing of flowering.

* * * * *

UNITED STATES PATENT AND TRADEMARK OFFICE
CERTIFICATE OF CORRECTION

PATENT NO. : 6,670,526 B1
DATED : December 30, 2003
INVENTOR(S) : Coupland, George M.

It is certified that error appears in the above-identified patent and that said Letters Patent is hereby corrected as shown below:

<u>Title page,</u>
Item [73], Assignee, Plant Bioscience Limited, Norwhich (GB)
to read as -- Pioneer Hi-Bred International, Inc. Johnston, Iowa --

Signed and Sealed this

Fifteenth Day of June, 2004

JON W. DUDAS
*Acting Director of the United States Patent and Trademark Office*

```
                      SEQUENCE LISTING

<160> NUMBER OF SEQ ID NOS: 27

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 1
gactacctga gaagttggaa tg                                           22

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 2
gccactggtc caaggattca g                                            21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 3
gcaagatgca ctaagtatga g                                            21
```

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 4
gagtggtact tagtgatgc                                             19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 5
cgtagtccat ctcctgacag                                            20

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 6
gaagttgtca ctgctgcgtc ag                                         22

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 7
gtctcatagg cgtctttg                                              18

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 8
cataccagag cattcagaat c                                          21

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 9
cacaggatcc ttcaatcagc tcgtag                                     26

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Primer

```
<400> SEQUENCE: 10
gcgcccggga ttgattactc aatctct                                        27

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 11
ctcaatctct agagtttagt gg                                             22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 12
gcatcatact agtatcctca ac                                             22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 13
gttgaggata ctagtatgat gc                                             22

<210> SEQ ID NO 14
<211> LENGTH: 1569
<212> TYPE: DNA
<213> ORGANISM: Artificial Sequence
<220> FEATURE:
<221> NAME/KEY: CDS
<222> LOCATION: (100)..(1569)
<223> OTHER INFORMATION: Description of Artificial Sequence: cDNA from
      Arabidopsis thaliana

<400> SEQUENCE: 14
agaaccctaa tttcatgttc taggtgtctc tcgaatggtt ctcatctcat tgattactca    60
atctctaggg tttagtggtt catccaaatt cgtacccta atg ggt gcc gta gcg      114
                                              Met Gly Ala Val Ala
                                                1               5 atc aat cgt aaa cgc agc gac gaa tcc ttc aat ttc att aat caa caa    162
Ile Asn Arg Lys Arg Ser Asp Glu Ser Phe Asn Phe Ile Asn Gln Gln
            10                  15                  20 tca acc aac cct tta cga aat tca ccg tat ttc caa gct tcc aag aaa    210
Ser Thr Asn Pro Leu Arg Asn Ser Pro Tyr Phe Gln Ala Ser Lys Lys
        25                  30                  35 cga aga ttc tca ttc gct atg tct gaa gat tct ggt aag cca gcg tct    258
Arg Arg Phe Ser Phe Ala Met Ser Glu Asp Ser Gly Lys Pro Ala Ser
    40                  45                  50 tca aac cca aca att tcg agg att tca agg tac cct gat gct aaa gct    306
Ser Asn Pro Thr Ile Ser Arg Ile Ser Arg Tyr Pro Asp Ala Lys Ala
55                  60                  65 cct ctt aga cga gag att cat gct cct agt aga gga att ctt aga tat    354
Pro Leu Arg Arg Glu Ile His Ala Pro Ser Arg Gly Ile Leu Arg Tyr
70                  75                  80                  85
```

```
gga aag gca aaa tct aat gat tac tgc gaa aag gac gca aat ttc ttt      402
Gly Lys Ala Lys Ser Asn Asp Tyr Cys Glu Lys Asp Ala Asn Phe Phe
                 90                  95                 100 gtt cgt aag tat gat gat gca aag aga tca gct ttg gaa gct ttg aga      450
Val Arg Lys Tyr Asp Asp Ala Lys Arg Ser Ala Leu Glu Ala Leu Arg
             105                 110                 115 ttc gtt aat aaa ggt aaa gac ttt gtt gat ttg ggt gat gag gtt gaa      498
Phe Val Asn Lys Gly Lys Asp Phe Val Asp Leu Gly Asp Glu Val Glu
             120                 125                 130 aag gag gaa gtt gtt tct gat gat tca agt gtt caa gca att gaa gtt      546
Lys Glu Glu Val Val Ser Asp Asp Ser Ser Val Gln Ala Ile Glu Val
    135                 140                 145 att gat tgt gat gat gat gag gag aag aag aat ctt cag cct tcg ttt      594
Ile Asp Cys Asp Asp Asp Glu Glu Lys Lys Asn Leu Gln Pro Ser Phe
150                 155                 160                 165 tct tct ggt gtt act gat gtt aag aaa ggg gag aac ttt aga gtt gag      642
Ser Ser Gly Val Thr Asp Val Lys Lys Gly Glu Asn Phe Arg Val Glu
                 170                 175                 180 gat act agt atg atg ctg gat tcg ttg tcg tta gat aga gat gtc gat      690
Asp Thr Ser Met Met Leu Asp Ser Leu Ser Leu Asp Arg Asp Val Asp
             185                 190                 195 aat gat gct tcg agc ctc gaa gct tat aga aag ctt atg caa agt gcg      738
Asn Asp Ala Ser Ser Leu Glu Ala Tyr Arg Lys Leu Met Gln Ser Ala
             200                 205                 210 gag aag agg aat tca aag ttg gaa gct ttg ggt ttt gag att gtg ttg      786
Glu Lys Arg Asn Ser Lys Leu Glu Ala Leu Gly Phe Glu Ile Val Leu
    215                 220                 225 aat gag aag aag ttg tca ctg ctg cgt cag tct cgc cca aag act gtg      834
Asn Glu Lys Lys Leu Ser Leu Leu Arg Gln Ser Arg Pro Lys Thr Val
230                 235                 240                 245 gaa aag cgt gtt gag gtg cct cgt gaa cct ttt att cct ctc aca gaa      882
Glu Lys Arg Val Glu Val Pro Arg Glu Pro Phe Ile Pro Leu Thr Glu
                 250                 255                 260 gat gaa gag gct gaa gtc tac cgt gcc ttt tct ggg aga aat aga agg      930
Asp Glu Glu Ala Glu Val Tyr Arg Ala Phe Ser Gly Arg Asn Arg Arg
             265                 270                 275 aag gtc ttg gct act cat gaa aac tca aac att gat att act gga gaa      978
Lys Val Leu Ala Thr His Glu Asn Ser Asn Ile Asp Ile Thr Gly Glu
             280                 285                 290 gtt ctg caa tgc ctt aca cca tct gca tgg cta aac gac gag gtt atc     1026
Val Leu Gln Cys Leu Thr Pro Ser Ala Trp Leu Asn Asp Glu Val Ile
    295                 300                 305 aat gtc tac ctt gaa cta ctc aaa gaa aga gaa act aga gag ccc cca     1074
Asn Val Tyr Leu Glu Leu Leu Lys Glu Arg Glu Thr Arg Glu Pro Pro
310                 315                 320                 325 aag tat ttg aag tgt ctc tac ttc aat acc ttt ttc tac aaa aag ctg     1122
Lys Tyr Leu Lys Cys Leu Tyr Phe Asn Thr Phe Phe Tyr Lys Lys Leu
                 330                 335                 340 gta agc gat tct ggt tat aat ttt aaa gct gtc agg aga tgg act acg     1170
Val Ser Asp Ser Gly Tyr Asn Phe Lys Ala Val Arg Arg Trp Thr Thr
             345                 350                 355 cag aga aag ttg gga tat gct ctt att gac tgt gac atg ata ttt gtt     1218
Gln Arg Lys Leu Gly Tyr Ala Leu Ile Asp Cys Asp Met Ile Phe Val
             360                 365                 370 ccc atc cac agg ggt gtg cat tgg acc ttg gca gta att aac aac agg     1266
Pro Ile His Arg Gly Val His Trp Thr Leu Ala Val Ile Asn Asn Arg
375                 380                 385 gaa agc aag ctc ttg tat ctt gat tca ctg aat gga gtt gat cct atg     1314
Glu Ser Lys Leu Leu Tyr Leu Asp Ser Leu Asn Gly Val Asp Pro Met
```

-continued

```
                390                 395                 400                 405
att ctg aat gct ctg gca aaa tac atg ggt gat gaa gca aat gaa aaa       1362
Ile Leu Asn Ala Leu Ala Lys Tyr Met Gly Asp Glu Ala Asn Glu Lys
                410                 415                 420 agt gga aaa aag att gat gct aat tcg tgg gac atg gaa ttt gtg gaa       1410
Ser Gly Lys Lys Ile Asp Ala Asn Ser Trp Asp Met Glu Phe Val Glu
            425                 430                 435 gac ctt ccc caa caa aag aat ggg tat gac tgt gga atg ttt atg ctt       1458
Asp Leu Pro Gln Gln Lys Asn Gly Tyr Asp Cys Gly Met Phe Met Leu
        440                 445                 450 aag tac atc gat ttt ttc agc aga ggc ctg ggg cta tgt ttc agc cag       1506
Lys Tyr Ile Asp Phe Phe Ser Arg Gly Leu Gly Leu Cys Phe Ser Gln
    455                 460                 465 gaa cac atg cca tac ttc cga ctc aga aca gct aaa gag att ctg agg       1554
Glu His Met Pro Tyr Phe Arg Leu Arg Thr Ala Lys Glu Ile Leu Arg
470                 475                 480                 485 cta cga gct gat tga                                                    1569
Leu Arg Ala Asp
```

<210> SEQ ID NO 15
<211> LENGTH: 489
<212> TYPE: PRT
<213> ORGANISM: Arabidopsis thaliana

<400> SEQUENCE: 15

```
Met Gly Ala Val Ala Ile Asn Arg Lys Arg Ser Asp Glu Ser Phe Asn
 1               5                  10                  15

Phe Ile Asn Gln Gln Ser Thr Asn Pro Leu Arg Asn Ser Pro Tyr Phe
                20                  25                  30

Gln Ala Ser Lys Lys Arg Arg Phe Ser Phe Ala Met Ser Glu Asp Ser
            35                  40                  45

Gly Lys Pro Ala Ser Ser Asn Pro Thr Ile Ser Arg Ile Ser Arg Tyr
        50                  55                  60

Pro Asp Ala Lys Ala Pro Leu Arg Arg Glu Ile His Ala Pro Ser Arg
65                  70                  75                  80

Gly Ile Leu Arg Tyr Gly Lys Ala Lys Ser Asn Asp Tyr Cys Glu Lys
                85                  90                  95

Asp Ala Asn Phe Phe Val Arg Lys Tyr Asp Ala Lys Arg Ser Ala
                100                 105                 110

Leu Glu Ala Leu Arg Phe Val Asn Lys Gly Lys Asp Phe Val Asp Leu
            115                 120                 125

Gly Asp Glu Val Glu Lys Glu Val Val Ser Asp Ser Ser Val
        130                 135                 140

Gln Ala Ile Glu Val Ile Asp Cys Asp Asp Glu Glu Lys Lys Asn
145                 150                 155                 160

Leu Gln Pro Ser Phe Ser Ser Gly Val Thr Asp Val Lys Lys Gly Glu
                165                 170                 175

Asn Phe Arg Val Glu Asp Thr Ser Met Met Leu Asp Ser Leu Ser Leu
                180                 185                 190

Asp Arg Asp Val Asp Asn Asp Ala Ser Ser Leu Glu Ala Tyr Arg Lys
            195                 200                 205

Leu Met Gln Ser Ala Glu Lys Arg Asn Ser Lys Leu Glu Ala Leu Gly
        210                 215                 220

Phe Glu Ile Val Leu Asn Glu Lys Lys Leu Ser Leu Leu Arg Gln Ser
225                 230                 235                 240

Arg Pro Lys Thr Val Glu Lys Arg Val Glu Val Pro Arg Glu Pro Phe
```

```
                        245                 250                 255
        Ile Pro Leu Thr Glu Asp Glu Ala Glu Val Tyr Arg Ala Phe Ser
                        260                 265                 270

Gly Arg Asn Arg Lys Val Leu Ala Thr His Glu Asn Ser Asn Ile
                        275                 280                 285

Asp Ile Thr Gly Glu Val Leu Gln Cys Leu Thr Pro Ser Ala Trp Leu
                        290                 295                 300

Asn Asp Glu Val Ile Asn Val Tyr Leu Glu Leu Leu Lys Glu Arg Glu
        305                 310                 315                 320

Thr Arg Glu Pro Pro Lys Tyr Leu Lys Cys Leu Tyr Phe Asn Thr Phe
                            325                 330                 335

Phe Tyr Lys Lys Leu Val Ser Asp Ser Gly Tyr Asn Phe Lys Ala Val
                        340                 345                 350

Arg Arg Trp Thr Thr Gln Arg Lys Leu Gly Tyr Ala Leu Ile Asp Cys
                        355                 360                 365

Asp Met Ile Phe Val Pro Ile His Arg Gly Val His Trp Thr Leu Ala
                        370                 375                 380

Val Ile Asn Asn Arg Glu Ser Lys Leu Leu Tyr Leu Asp Ser Leu Asn
        385                 390                 395                 400

Gly Val Asp Pro Met Ile Leu Asn Ala Leu Ala Lys Tyr Met Gly Asp
                            405                 410                 415

Glu Ala Asn Glu Lys Ser Gly Lys Lys Ile Asp Ala Asn Ser Trp Asp
                        420                 425                 430

Met Glu Phe Val Glu Asp Leu Pro Gln Gln Lys Asn Gly Tyr Asp Cys
                        435                 440                 445

Gly Met Phe Met Leu Lys Tyr Ile Asp Phe Phe Ser Arg Gly Leu Gly
                        450                 455                 460

Leu Cys Phe Ser Gln Glu His Met Pro Tyr Phe Arg Leu Arg Thr Ala
        465                 470                 475                 480

Lys Glu Ile Leu Arg Leu Arg Ala Asp
                            485

<210> SEQ ID NO 16
<211> LENGTH: 10478
<212> TYPE: DNA
<213> ORGANISM: Arabidopsis thaliana

<400> SEQUENCE: 16
accaaaaaaa tttaccctat gatctattat atatgaaacc atatttctag aaaaatttga      60
tttcttaatg ttttgtgttc atatatttta tgattttaca tagatattaa agaaatagac     120
agaataaata tatttagtca cgtaaagtat tggaataatt aatgtatttg atttcactta     180
ggatctctaa tctatttcac taggattttc tttcatggtt gggttggcac tggcctttga     240
gataagatac gcattcgtgt ttggatgatg ttacctttcc acgcattgaa caagagctgc     300
aacttcagaa acattaccgt atctatcaca cgtgtcatca acaagggtga agactgtgtt     360
gatcttagct agtgaaactc tcccaagtga aaattgtggc tcgaaatata tcattattgc     420
aaataaatag cattcgatca atctatccct gaagtaaggt gggagtttag atgcaaggtc     480
ttgctgcttc caccatctgc aaaacatgtc aatgactatt gtcaacttgt atcgcaaaaa     540
acatatagct agaagcacga aaaatctaga gtatagtact tggtcagagt tttcaattct     600
tgaatccaat ttagctgcaa aaacttgaaa ttgatcttgg caaatctaag tagcatcttg     660
ttgtgatctt cttcttgttc atagaaagaa atgtattccc tcgcgaatat catttcggca     720
```

-continued

| | |
|---|---|
| ttgtaatgtt gaggcatgca aagagcattt cgtatacgca ttaagatatg gggagaactt | 780 |
| gctccagctc tagctaacga ctccaagttt cttgtagtga agcttaacgc ttcctccaag | 840 |
| atatcttctc ttgttgtcct taagtgagca gcttcataca aactcaccat gcccttgaca | 900 |
| tcactggtta tagattccat aaactttca ttctcccctt tgaatctctt gaaaacatct | 960 |
| attggtcaat aggagaatct tgttaataca tatgaatcga ttacaaaaaa atgtactggt | 1020 |
| agataacttt taccggtaga catgttgtaa ccgtatgtcc tgaaacccca aacatgatg | 1080 |
| gaaatcgtgt acaaatcatc ttcaccggct atcatctcct gtatcttttc aaaaccctct | 1140 |
| tctagactct gctcaatctc atcttcaaag tgaaacgcta caccaaggct cacaagcata | 1200 |
| tatatgaaaa gaatcctctt cttggtcgac tcaatgcttt tcgaagaaaa catgagcatc | 1260 |
| tcccctactt ccggctttag tctctcaatc tcttgggcaa gggcattcat ttcctaacaa | 1320 |
| taatatcata tgttcatacc cgttacatcg atcttttaca tttattatat atatgtttgt | 1380 |
| cagtgtgtat tatagactca ccgagacatc aacttgagca gagaggaaat ggtgacccca | 1440 |
| ttttgaaagc ggcagtctct tgaacttgcg attactttct tgatcatgac aggcccgagt | 1500 |
| agggtggcc ttcatgcgaa caagctttcc atgctgacct gaaaatgact tgtggggaaa | 1560 |
| gctagagagt tttcttaccg aaaataaatt ggaacgtaaa ggaagagaga gtatagatcc | 1620 |
| ataagctgat atgcattgca tgtttactac tagtgatatg gaatacattt tcaccaccaa | 1680 |
| atttataggc aaaacataag cgttttcatt aagtcatctt ttgaaaagtt ttggaagaat | 1740 |
| gtatattaat accccccatat ttatcttctt cagtgtataa tacaacctat gttgggacca | 1800 |
| tgatattttc tgaatttata gtgatattag tttatctta aattgatatt tattaatcta | 1860 |
| tatagatctt ttttaatta tttaattttt taaagaatac gagttgacac aattcaatat | 1920 |
| acatcaaatt aatgacttgg atgttgaaat ttgtgtagta ttagaattga aaatttaata | 1980 |
| tttcaaaaaa ctcatttgac aataaatcac aatgactata actgaattca tttatataat | 2040 |
| agatatacat acatctaagt ttatgattaa taacctcaac tatcagattt ttaaatgtag | 2100 |
| tagactattg aaatgaaaat aatgcagatt aagaagttgt atacttataa aaacttatga | 2160 |
| ctaattgtat taggaagtta taaacgatac tacaatatga tagttttaaa acacaacata | 2220 |
| atttaatgaa aattagagac aaaatcattg tttgatgtaa taatagttca agacaaactc | 2280 |
| taacaaacat tcaatagttc aaaaaatatt taaactatag attatatata ttatcgtata | 2340 |
| tatattatat ttttgtggtt attaatttat gatgttatta aaatcatatt ttttatatag | 2400 |
| ggttttaaaa aattgttaac ttattatttt atcaaattat gttaaatttt acattcacac | 2460 |
| gacttgaaac taatataata ttatctcctt gtatttatta atttatcaaa aattaatttg | 2520 |
| tagaggtttt actgtaaaac atgtttagtt tttcatttt taaaaaacct ccaagtggca | 2580 |
| aaaataagat ccatctccat ctaaaaaagt gcaaacaaat ctccatcatt taaaaatcaa | 2640 |
| cgttaacatc catatctatt gttgttgttt tttacttctt tttctcttgg tcaaactcta | 2700 |
| cgttagtttg atcaataaat atgacaagaa tttttgcagt ctcataggcg tctttgtaaa | 2760 |
| ggttagttag cgtctacata attttccgaa agatataatt ttcttgagat acagttaact | 2820 |
| caattactga aatgtaataa ctttctaaaa gttgtggcta ttaaacaaaa ttgtgaaaaa | 2880 |
| atttaaacca aaagccactt caaaaacaaa gaaaaccata accattaatc aaaattcttt | 2940 |
| ttttttttgtt aacaagtact agttgcatta aattgtaaac atatggtggt gttgtatatg | 3000 |
| tttgatacaa agaacctata taacaaaggc ttgttgggat agtgcatctg ccacattatt | 3060 |
| tcttttccga ttgacatgtc catagatgag tgtgatagct tcaacatcca atatcgtata | 3120 |

```
ccaccaaaga ctgaagagta gtaccaagaa tatttatata tatatttatt tatttattta    3180
ttttggtaag gagaatattt atatcatgat cccaccatac tttaattgtt atgaaaaaat    3240
tttaatttga ttttcataaa ttttatagtt tagttaagta taaaaccaca attttttttc    3300
tttcaaatat tattttttgga gaaaacccccc aaatttaaaa ggaaagagaa aaaatcaaat   3360
cattcatctt tgagctttct tttcttctac agaaccctaa tttcatgttc taggtgtctc    3420
tcgaatggtt ctcatctcat tgattactca atctctaggg tttagtggtt catccaaatt    3480
cgtaccctaa tgggtgccgt agcgatcaat cgtaaacgca gcgacgaatc cttcaatttc    3540
attaatcaac aatcaaccaa ccctttacga aattcaccgt atttccaagc ttccaagaaa    3600
cgaagattct cattcgctat gtctgaagat tctggtaagc cagcgtcttc aaacccaaca    3660
atttcgagga tttcaaggta ccctgatgct aaagctcctc ttagacgaga gattcatgct    3720
cctagtagag gaattcttag atatggaaag gcaaaatcta atgattactg cgaaaaggac    3780
gcaaatttct tgttcgtaa gtatgatgat gcaaagagat cagctttgga agctttgaga     3840
ttcgttaata aggtaaaga ctttgttgat ttgggtgatg aggttgaaaa ggaggaagtt     3900
gtttctgatg attcaagtgt tcaagcaatt gaagttattg attgtgatga tgatgaggag    3960
aagaagaatc ttcagccttc gttttcttct ggtgttactg atgttaagaa aggggagaac    4020
tttagagttg aggatactag tatgatgctg gattcgttgt cgttagatag agatgtcgat    4080
aatgatgctt cgagcctcga agcttataga aagcttatgc aaagtgcgga gaagaggaat    4140
tcaaagttgg aagctttggg ttttgagatt gtgttgaatg agaagaagtt gtcactgctg    4200
cgtcagtctc gcccaaagac tgtggaaaag cgtgttgagg tgatgagatt tatactaatc    4260
tttcttgaat tggatataat taatgacatt gctttgtttg gattgtttct ctaaaatgca    4320
tatgatgtta tcgcctactg tttgttagtg tagactgaag atagtacaat acttgttggc    4380
tttattggtt attaagctgc agttattact tatgcacaca gagtcaaagt tcttctactt    4440
attagagtat attgtaatct tagcgttgag atcgttagtg tgtttctatg tttattgttg    4500
ttgttaacac tatgtttgtt gttgatataa tgaaggtgcc tcgtgaacct tttattcctc    4560
tcacagaaga tgaagaggct gaagtctacc gtgccttttc tgggagaaat aggtatggtt    4620
cttaagacct ctagcatgtt gagtgatttt ttttagtcta accaaaaacc aaatgtctcc    4680
cattttcaga aggaaggtct tggctactca tgaaaactca acattgata ttactggaga    4740 acttctgcaa tgccttaccc atctgcatgg ctaaacacaa gtacacttgt ccataatatc    4800
tacacataaa ctctaaacca tttctttgtg atttcttgtt ctgttttata ggttatcaat    4860
gtctaccttg aactactcaa agaaagagaa actagagagc ccaaaaagta tttgaagtgt    4920
cactacttca ataccttttt ctacaaaaag gtttgttttc tttctgctca gatgattttt    4980
aacaaaaatt tgatcctttt tgcctcatgt cagttcgact gagtagctgc tacttgcttc    5040
cataaaaatg ataagcagta tgtttaagtg atctttatga taagattatt gatatatttg    5100
gccttgtttc tccccatggt actcagttgt ctctggcttc tgtatcccat ggaatggcag    5160
tgagtaacca agacaagctg tggccttctt atacgttgat gaatcctctg gcacttaaat    5220 ctgtcttttct ttaattattt ttttcagctg gtaagcgatt ctggttataa ttttaaagct   5280
gtcaggagat ggactacgca gagaaagttg ggatatgctc ttattgactg tgacatggta    5340
attttgtcga agaacctgaa tttgaagatt ctcttgttaa tattacgcat gtagtccaat    5400
ttatttatgt ttaacttagt ctgtgccctc tgcagatatt tgttcccatc cacagggtg    5460
```

-continued

```
tgcattggac cttggcagta attaacaaca gggaaagcaa gctcttgtat cttgattcac    5520
tgaatggagt tgatcctatg attctgaatg ctctggtatg atttaatttc taactcttat    5580
tcgctttatt tagtctatta ataactgaca tgttggatgc attaaaagat attagatgct    5640
gataaatctt tatcatcatt tcttgattct gaaatctgtt tggagacatt atggagatgc    5700
cagaagctgt tattgctttt taaatcggac actactgtga aagtgttcta accatatata    5760
ctagtcgtta tagctaatgc cagatctgat attctgcttc aggcaaaata catgggtgat    5820
gaagcaaatg aaaaaagtgg aaaaaagatt gatgctaatt cgtgggacat ggaatttgtg    5880
gaagaccttc cccaacaaaa gaatgggtat gtaactatgc ttgaacttgc tatgatccat    5940
gatcatgtga aaggaactat cttgttaaag agataacctc tgtagaatca gatacttgtc    6000
ttctgatgtg ggaatatggg ttttttaagac aaaggataga tctggtttga gattgattag    6060
gagaaattca cctgatataa attttgataa tggaatcaac aagggtataa cttaactgtt    6120
cttatgctct ttagcactct ggttaagctc tctgctaact ctatattgtt tctttgttgc    6180
aatcttttat attctcaggt atgactgtgg aatgtttatg cttaagtaca tcgattttt    6240 cagcagaggc ctggggctat gtttcagcca ggtaagctat cagaatccaa atctctgaat    6300
gcctcaagaa actgtagttg agaataaaaa ctggttgtct tgaaacaata tggaattagt    6360 atatcccccct agcagtttat gtaacttgta ggatttaggc atttagcgta ataacattgt    6420
attactttgc aggaacacat gccatacttc cgactcagaa cagctaaaga gattctgagg    6480
ctacgagctg attgaagttg cttgtgctaa tgtttttttcg gctattagga atactatttt    6540
tggttgccat tgttgatttg ttcaaacttt aaatcccact cctttttaggc agtgaagcac    6600 tcggctttaa aagcagaggt aaaaactgag tcaagcccag agctcttagc tcgttccgtt    6660
attgtatttt tttccttctt cttgttttaa aatgtagatg aagcgttttg gatctctatg    6720
ttggttagtc tagctgaaga tatatgagat gttgaaaacc ttatttattt ctctccggtc    6780
ttgaccagtg cgaacgcaat ttaaagtttc catctagtat cggttcgata tattttcctc    6840
tgttcaatag ccaaaattcc atgaataatc tcttgaaagc aaatgttttc gatatacaaa    6900
tgttctgcac aatttcccca atacatacac gaatatgtta caaatataca acaaactgct    6960
gtttgtgagt acaaatgttg acaaggacag aaaaaaaca aatcccaaa tgtaacattg    7020 acatattaaa acccactccc aaaaacaaaa acaaattccc caattcataa aacacgagag    7080
gaaggaagac ttgtgtgtat ctcctaacaa aaactgactg gaaggcaaac taacttccac    7140
tgcctttcct agcgcggaac tctcttccgg ctaagtatct cctgttcttt cagacggtgt    7200
tggaaccgag caagacgggc ttgaagactt acaagaccag ctgctttacg ggacaacaca    7260
aagctcagct gtgtaacata gttgtcaatc atgctccctg gccgatccac cttcgctagt    7320
aatttcattt cctacaaaaa aaacatgaa ataatgttaa aacaatcaca agacatatga    7380
gccataacct cgtgaactat ttccattgta tcctcgatct cttttctgtg tgctgtaatt    7440 aagtctctctt cttcctgcca gagtttaaac aaaataatta ccatattaca ggttttctaa    7500
ggttattcgt gagcgatatt cataaaattc cctcacgctc atagcataat ttagaagtat    7560
agaagggtca aatggctctt tacctcaagc aatgcatcaa tgttttcatc aagagaaggc    7620
tccgttgttt catactgcct tgaagatgta tcgcttgtgt tctgactgct agccatattt    7680
tgttgtctag aatttgtcat ggcagggaca tcagtcttga gaataagatg agtgaatcct    7740
ttgactagtg gagccgccaa aagaagattt taaaatgtta agcataaatc atattcctta    7800
aatgttaagt gaatcctttg actagtatag tatagtgtct ggtttttcat tagactttct    7860
```

```
gagatgagag gtatttctat taaaacttaa gttgaaggtt ttaaaatgaa tcagccaaaa    7920
ctgcagggtt tgtttcatta aaatcccaaa attgtttcgt atacatcata ttacccactg    7980
aggactctgc tctttgtgga aatgctaaat tagccccaaa ccttttttcta agtcccactt    8040 tgaattctaa taagaacgaa cagatcgcgg gaaatccaaa atgatttgaa acctttttcac   8100 ctgaatttct gtgaaatcca aaattctctc tctatcagta gagaatcgcc atggatgaag    8160
agcttctgct cactagaatc cttgcaggaa tcgaaggagg agacgatgaa tctgactatc    8220
atgaactcgt cacggatctc aaatctctac ttgatacaga cgatgatgaa attctcaatc    8280
gattctacgg tagtctctcc tcaatggctt cttcgtttct ccgctgtatc tccgccgcca    8340
tggattctcc ggttgaatca ggccgtcttg ctattttagc ctccgacgct tatctcagtc    8400
tgcttctttc cacgaattgc cccgttttca ctttcttctc tccgattgcg tttctttctc    8460
tacttggctc aattcgccgc tacctcaaac gccgtgatga ttccgccggt caagggagta    8520
attcgcagcg agagaaaggg aataagaaga agagaggacg tggtaagagg aatttagggt    8580
atgaagatgg ggaagagact gaagaaggtg gatttgatgc gaaattgatg tttatagtgt    8640
tagagaagct tggctcggtt ctgagttttg ttcatttaga tagatttcct gatagtttga    8700
aatctttggt acaaactgtg agtgagattc ctttattggc gttggagcac tctggagttt    8760
tgaattatga tcgattgatg gaaatgtgtg ggaagattct gggaggagtg ttgaattctg    8820
accatggaga tatggcactc actgctgctg agatttcaaa gtctttgaca ccgttgcttc    8880
ttatggggaa acatcaagcg agaagttttg cgttgggatt tgtgtcaagg aaattgatga    8940
gtttggctaa agataaccct gaattgaaaa agttgtgtc taatttgcct aagtttctgg     9000
ttcataaggc acctgagaag gccgagccgc gtggatttgc agtggaggcg gtactggaga    9060
ttgtaaaggc aatggaggtt gagggccaat cagagtttgt tgattttgta atgaagatgt    9120
gtcaagggaa gtctaatttt agagtattag ctgttgatat tatacctctg ttgataagct    9180
cattaggaaa ccctctagga gatattagtt cagagaatgg gttgaaagat tcgtggggct    9240
tgggttgtat tgatgcttta gttcagcggt gttcagacac gagcgctttg attagagctc    9300
gagctttgtc caacttggct caagttgtgg agttcttgtc tggtgatgaa aggagtaggt    9360
cgatcctgaa acaagccctt gggtttaacg gtgagacttc agagggaaaa ggtgcagtaa    9420
ctgacctttt gaagaaaaga tgtgtggatg agaaggcggc tgtaaggaga gcagctcttc    9480
ttctggtgac aaaattgaca tcgcttatgg gtggttgctt tgatggtagt atcctaaaga    9540
caatgggtac atcttgttct gatccgctaa taagtataag aaaggctgca gtttcagcta    9600
tttccgaggt atgttttctg taactcagtt tcttctttct catttacccg atggtaatat    9660
gtgtagagtt agtataattt atacgggttt gctttgacct taattagctc aaagttaaag    9720
agaccaaatg tgcaagccaa aaatgttttt agatgaatga atgggaaatt acatagcaac    9780
tgcttccgtc ggtttcatac taaaatcaga taatctttat actttaactt atccctgaat    9840
ataggtcagg cactcaggct aatgacttgt tatcatattt ctctgatgat gcaagttcat    9900
tgtcttctgt tcactgtagg cattcagaat atgtacagat gaaattgtga ccactgaatg    9960
gttacattct gttcctcgga tgatcatgga caatgaaact agcatccaag aagaatgcga   10020
gaatgtcttt catgaattag ttctggagag aatattacga gctggaaatg tgctttctcc   10080
agacagtgct tctctcccta acaaccggaa cactacttca aaagatctag acagagacat   10140
tgaagccttg tttccagaag gagttttggt tctcttaagg gagctttgca acagtgaggt   10200
```

```
ttctccttgg gttacgaaaa tatgtggaag tttgggaaag aagaagcgac taaaaccaag   10260
agttgccctt gcgcttcagt gtatcataaa ggaatctgaa tcactgtggt tgagtcgttc   10320
aatgccaata aatagatgga cagctcctgc tggtgcttgg ttccttctat cagaggtttc   10380
agtttatctt tcaaagtctg tcgaatggga atttcttcac catcattggc agttgcttga   10440
caagaatgac gtacaaggtt tgtcagaatt ctgtttat                           10478
```

<210> SEQ ID NO 17
<211> LENGTH: 12
<212> TYPE: PRT
<213> ORGANISM: Homo sapiens

<400> SEQUENCE: 17

His Phe Met Tyr Ser Val Leu Ser Ser Ile Leu Asn
 1               5                  10

<210> SEQ ID NO 18
<211> LENGTH: 7
<212> TYPE: PRT
<213> ORGANISM: Homo sapiens

<400> SEQUENCE: 18

Ser Leu Gly Val Thr Lys Gln
 1               5

<210> SEQ ID NO 19
<211> LENGTH: 135
<212> TYPE: PRT
<213> ORGANISM: Homo sapiens
<220> FEATURE:
<221> NAME/KEY: SITE
<222> LOCATION: (2)
<223> OTHER INFORMATION: Xaa is Unknown

<400> SEQUENCE: 19

Asn Xaa Trp Thr Lys Gly Val Asn Leu Phe Glu Gln Glu Ile Ile Leu
 1               5                  10                  15

Val Pro Ile His Arg Lys Val His Trp Ser Leu Val Val Ile Asp Leu
                20                  25                  30

Arg Lys Lys Cys Leu Lys Tyr Leu Asp Ser Met Gly Gln Lys Gly His
         35                  40                  45

Arg Ile Cys Glu Ile Leu Leu Gln Tyr Leu Gln Asp Glu Ser Lys Thr
     50                  55                  60

Lys Arg Asn Ser Asp Leu Asn Leu Leu Glu Trp Thr His His Ser Met
 65                  70                  75                  80

Lys Pro His Glu Ile Pro Gln Gln Leu Asn Gly Ser Asp Cys Gly Met
                 85                  90                  95

Phe Thr Cys Lys Tyr Ala Asp Tyr Ile Ser Arg Asp Lys Pro Ile Thr
            100                 105                 110

Phe Thr Gln His Gln Met Pro Leu Phe Arg Lys Lys Met Val Trp Glu
        115                 120                 125

Ile Leu His Gln Gln Leu Leu
    130                 135

<210> SEQ ID NO 20
<211> LENGTH: 37
<212> TYPE: PRT
<213> ORGANISM: Homo sapiens
<220> FEATURE:
<221> NAME/KEY: SITE
<222> LOCATION: (20)

<223> OTHER INFORMATION: Xaa is Unknown

<400> SEQUENCE: 20

Glu Asn Phe Ala Trp Ser Ser Cys Trp Trp Phe His Arg His
1               5                   10                  15

Phe His Ile Xaa Ser Cys Met Trp Val Lys Lys Ser Leu His His Phe
            20                  25                  30

Cys Ser His Arg Tyr
            35

<210> SEQ ID NO 21
<211> LENGTH: 77
<212> TYPE: PRT
<213> ORGANISM: Mus sp.

<400> SEQUENCE: 21

Leu Asn Ile Leu Leu Val Pro Ile His Leu Gly Val His Trp Cys Leu
1               5                   10                  15

Ala Val Val Asp Phe Arg Arg Lys Ser Ile Thr Tyr Tyr Asp Ser Met
            20                  25                  30

Gly Gly Ile Asn Asn Glu Ala Cys Arg Ile Leu Leu Gln Tyr Leu Lys
        35                  40                  45

Gln Glu Val Leu Thr Arg Lys Gly Lys Ser Leu Thr Pro Met Ala Ser
    50                  55                  60

Ser Ser Ser Ala Arg Arg Ala Arg Lys Ser His Ser Arg
65                  70                  75

<210> SEQ ID NO 22
<211> LENGTH: 47
<212> TYPE: PRT
<213> ORGANISM: Mus sp.

<400> SEQUENCE: 22

Met Gly Val Leu Trp Met Phe Ala Cys Lys Tyr Ala Asp Cys Ile Thr
1               5                   10                  15

Lys Gly Arg Pro Ser Leu His Thr Gly Asn Thr Cys His Ile Ser Gly
            20                  25                  30

Arg Arg Met Val Trp Glu Phe Leu Thr Gly Ala Leu Val Lys Phe
        35                  40                  45

<210> SEQ ID NO 23
<211> LENGTH: 209
<212> TYPE: PRT
<213> ORGANISM: Oryza sativa
<220> FEATURE:
<221> NAME/KEY: SITE
<222> LOCATION: (70)
<223> OTHER INFORMATION: Xaa is Unknown
<221> NAME/KEY: SITE
<222> LOCATION: (198)
<223> OTHER INFORMATION: Xaa is Unknown

<400> SEQUENCE: 23

Arg Leu Gly Phe Glu Gln Leu Ala Asp Val Leu Pro Arg Phe Gly Pro
1               5                   10                  15

Arg Lys Glu Asp Glu Pro Phe Val Pro Phe Thr Asp Glu Asp Glu Asp
            20                  25                  30

Ser Val Asp His Ala Leu Gly Gly Arg Asn Arg Arg Glu Arg Leu Val
        35                  40                  45

Val His Glu Ser Ser Asn Ile Val Ile Thr Arg Glu Thr Leu Gln Cys
    50                  55                  60

-continued

```
Leu Asn Glu Thr Glu Xaa Leu Asn Asp Glu Val Ile Asn Leu Tyr Leu
 65                  70                  75                  80

Glu Leu Leu Lys Glu Arg Glu Leu Arg Glu Pro Asn Lys Phe Leu Lys
             85                  90                  95

Cys His Phe Phe Asn Thr Phe Phe Tyr Lys Lys Leu Ile Thr Gly Gly
                100                 105                 110

Tyr Asp Tyr Lys Ser Val Arg Arg Trp Thr Thr Lys Arg Lys Leu Gly
            115                 120                 125

Tyr Ser Leu Leu Glu Cys Asp Lys Ile Phe Val Pro Ile His Lys Glu
130                 135                 140

Val His Trp Cys Leu Ala Val Ile Asn Ile Arg Asp Lys Lys Phe Gln
145                 150                 155                 160

Phe Leu Asp Ser Leu Gly Ser Met Asp Met Lys Ala Leu Arg Thr Leu
                165                 170                 175

Ala Arg Tyr Leu Val Asp Glu Val Lys Asp Lys Ser Gly Gln His Ile
            180                 185                 190

Asp Ala Leu Ser Trp Xaa Gln Glu Gly Val Lys Asn Leu Pro Leu Gln
            195                 200                 205

Glu

<210> SEQ ID NO 24
<211> LENGTH: 211
<212> TYPE: PRT
<213> ORGANISM: Caenorhabditis elegans

<400> SEQUENCE: 24

Arg Lys Arg Leu Glu Leu Gln Gly Ile Ala Ile Arg Pro Lys Val Glu
  1               5                  10                  15

Lys Lys Lys Val Asp Asp Phe Met Ala Leu Pro Asp Ala Ala Asp Ala
             20                  25                  30

Leu Val Glu Arg Ala Trp Ser Gly Gly Asn Pro Asn Glu Gln Phe Val
         35                  40                  45

Asp Ala Phe Ser Ile Gln Ile Cys Lys Lys Asp Leu Ala Thr Leu Ser
 50                  55                  60

Gly Leu His Trp Leu Asn Asp Glu Ile Ile Asn Phe Tyr Leu Gln Leu
 65                  70                  75                  80

Ile Cys Asp Arg Ser Asn Gly Asp Ser Lys Tyr Pro Lys Ile Tyr Ala
             85                  90                  95

Phe Asn Thr Phe Phe Tyr Ser Asn Ile Val Ser Lys Gly Tyr Ala Ser
                100                 105                 110

Val Lys Arg Trp Thr Arg Lys Val Asp Ile Phe Ala Phe Asp Ile Val
            115                 120                 125

Leu Val Pro Val His Leu Gly Met His Trp Cys Met Ala Val Ile Asp
130                 135                 140

Met Gly Glu Lys Lys Ile Glu Phe Tyr Asp Ser Leu Tyr Asp Gly Asn
145                 150                 155                 160

Thr Ala Val Leu Pro Ala Leu Arg Gly Tyr Leu Glu Ala Glu Ser Leu
                165                 170                 175

Asp Lys Lys Lys Thr Ala Met Asn Phe Ser Gly Trp Thr Ile Gln Gln
            180                 185                 190

Met Thr Lys Ser Arg Ser Phe Leu His Tyr Pro Lys Tyr Arg Cys Asp
            195                 200                 205

Ser His His
        210
```

<210> SEQ ID NO 25
<211> LENGTH: 631
<212> TYPE: DNA
<213> ORGANISM: Oryza sativa
<220> FEATURE:
<221> NAME/KEY: misc_feature
<222> LOCATION: (212)
<223> OTHER INFORMATION: n is a or g or c or t
<221> NAME/KEY: misc_feature
<222> LOCATION: (594)
<223> OTHER INFORMATION: n is a or g or c or t

<400> SEQUENCE: 25

```
gccgcctcgg ctttgagcag ctcgccgatg tcctcccacg gttcgggccc cggaaggagg    60
atgaaccttt tgttccttt  acggatgagg atgaggatag tgttgatcat gctcttggtg   120
gccgtaacag acgtgaaagg ctagtggtac atgaatcatc aaatattgtc ataacaagag   180
agaccttgca gtgcttgaac gaaacggagt gnctaaatga tgaggtcata aatttgtatc   240
ttgagctgct gaaagagagg gaactgagag aacctaacaa gttttgaaa tgccacttct    300
tcaatacctt tttctacaaa aagctcatta ctggtgggta tgattataag tctgtcagaa   360
gatggacaac taaaggaag  ttaggttaca gcctacttga atgtgataag atctttgttc   420
ctatacacaa ggaagtgcat tggtgtttag cagtcataaa cataagggac aaaaagtttc   480
aatttctgga ttcacttggc agcatggaca tgaaggcatt gagaacttta gcaaggtatc   540
ttgtagatga ggtgaaagat aagagtggcc aacatattga tgctctttca tggnagcagg   600
agggtgtaaa aaaccttcct ttgcaagaga a                                   631
```

<210> SEQ ID NO 26
<211> LENGTH: 595
<212> TYPE: DNA
<213> ORGANISM: Homo sapiens
<220> FEATURE:
<221> NAME/KEY: misc_feature
<222> LOCATION: (70)
<223> OTHER INFORMATION: n is a or g or c or t
<221> NAME/KEY: misc_feature
<222> LOCATION: (530)
<223> OTHER INFORMATION: n is a or g or c or t

<400> SEQUENCE: 26

```
gcacttcatg tattcagtac tttcttctat cctaaattaa agtctggggg ttaccaagca    60
gtgaaacgan tggaccaaag gggtaaatct ctttgaacaa gaaattattc tggtgcctat   120
tcatcggaag gtacattgga gcctggtggt gattgaccta agaaaaagt  gtcttaaata   180
tctggattct atgggacaaa agggccacag gatctgtgag attctccttc agtatttaca   240
ggatgaaagt aagaccaaaa gaaatagtga tctgaatctt ttagagtgga cccatcacag   300
catgaaacca cacgagattc ctcaacagct gaatgggagt gattgtggaa tgtttacttg   360
taaatatgca gattatattt ctagggacaa acctatcaca tttactcagc accagatgcc   420
tctcttccgg aagaagatgg tgtgggaaat ccttcatcag cagttgctgt gagaaaactt   480
tgcctggtcc tctagctgct ggtggttctt tcacagacat ttccatatan cctcatgcat   540
gtgggttaaa aagtccctgc atcacttctg ttctcacagg tactgagctg tcaaa        595
```

<210> SEQ ID NO 27
<211> LENGTH: 259
<212> TYPE: PRT
<213> ORGANISM: Arabidopsis thaliana

```
<400> SEQUENCE: 27

Glu Lys Lys Leu Ser Leu Leu Arg Gln Ser Arg Pro Lys Thr Val Glu
1               5                   10                  15

Lys Arg Val Glu Val Pro Arg Glu Pro Phe Ile Pro Leu Thr Glu Asp
            20                  25                  30

Glu Glu Ala Glu Val Tyr Arg Ala Phe Ser Gly Arg Asn Arg Arg Lys
            35                  40                  45

Val Leu Ala Thr His Glu Asn Ser Asn Ile Asp Ile Thr Gly Glu Val
            50                  55                  60

Leu Gln Cys Leu Thr Pro Ser Ala Trp Leu Asn Asp Glu Val Ile Asn
65                  70                  75                  80

Val Tyr Leu Glu Leu Leu Lys Glu Arg Glu Thr Arg Glu Pro Pro Lys
            85                  90                  95

Tyr Leu Lys Cys Leu Tyr Phe Asn Thr Phe Phe Tyr Lys Lys Leu Val
            100                 105                 110

Ser Asp Ser Gly Tyr Asn Phe Lys Ala Val Arg Arg Trp Thr Thr Gln
            115                 120                 125

Arg Lys Leu Gly Tyr Ala Leu Ile Asp Cys Asp Met Ile Phe Val Pro
            130                 135                 140

Ile His Arg Gly Val His Trp Thr Leu Ala Val Ile Asn Asn Arg Glu
145                 150                 155                 160

Ser Lys Leu Leu Tyr Leu Asp Ser Leu Asn Gly Val Asp Pro Met Ile
            165                 170                 175

Leu Asn Ala Leu Ala Lys Tyr Met Gly Asp Glu Ala Asn Glu Lys Ser
            180                 185                 190

Gly Lys Lys Ile Asp Ala Asn Ser Trp Asp Met Glu Phe Val Glu Asp
            195                 200                 205

Leu Pro Gln Gln Lys Asn Gly Tyr Asp Cys Gly Met Phe Met Leu Lys
            210                 215                 220

Tyr Ile Asp Phe Phe Ser Arg Gly Leu Gly Leu Cys Phe Ser Gln Glu
225                 230                 235                 240

His Met Pro Tyr Phe Arg Leu Arg Thr Ala Lys Glu Ile Leu Arg Leu
            245                 250                 255
Arg Ala Asp
```